(12) United States Patent
House et al.

(10) Patent No.: US 10,327,939 B2
(45) Date of Patent: Jun. 25, 2019

(54) DEVICES, SYSTEMS, AND METHODS FOR ADMINISTERING THERAPY

(71) Applicant: FalconWorks, Colorado Springs, CO (US)

(72) Inventors: J. Glen House, Colorado Springs, CO (US); Scott Rea, Colorado Springs, CO (US); Duncan H. Stewart, Colorado Springs, CO (US); Andrew Murrell, Bishopville, MD (US); Joshua Nielsen, Chevy Chase, MD (US); Kyung M. Kim, Duluth, GA (US); Ryan Mavity, Columbus, MS (US); Gregory M. Kabel, Danville, CA (US); Marcus E. Walker, Aurora, CO (US); John M. Davis, Goodfellow AFB, TX (US); Jonathan J. Schneider, Dorchester, MA (US); Brian S. Brookover, Columbus, MS (US); Chad Moore, Pagosa Springs, CO (US); Melissa VonOhlen, Colorado Springs, CO (US); Gage Owens, Enid, OK (US); Ryan Wallway, Grand Junction, CO (US); Colton Buechel, Shelton, WA (US); Haley Holcombe, Albuquerque, NM (US); Daniel Neal, Morgan Hill, CA (US)

( * ) Notice: Subject to any disclaimer, the term of this patent is extended or adjusted under 35 U.S.C. 154(b) by 467 days.

(21) Appl. No.: 14/865,895

(22) Filed: Sep. 25, 2015

(65) Prior Publication Data

US 2016/0089573 A1 Mar. 31, 2016

Related U.S. Application Data

(60) Provisional application No. 62/055,430, filed on Sep. 25, 2014.

(51) Int. Cl.
| | |
|---|---|
| *A61F 5/01* | (2006.01) |
| *G16H 15/00* | (2018.01) |
| *G16H 20/30* | (2018.01) |
| *G16H 40/63* | (2018.01) |

(Continued)

(52) U.S. Cl.
CPC .......... *A61F 5/0102* (2013.01); *G16H 15/00* (2018.01); *G16H 20/30* (2018.01); *G16H 40/63* (2018.01); *G16H 50/20* (2018.01); *G16H 50/30* (2018.01)

(58) Field of Classification Search
CPC ...... A61F 5/0102; G16H 20/30; G16H 40/63; G06F 19/3481
See application file for complete search history.

(56) References Cited

U.S. PATENT DOCUMENTS

| | | | | |
|---|---|---|---|---|
| 2012/0296235 A1* | 11/2012 | Rupp | .................. | A61B 5/1128 600/595 |
| 2013/0123667 A1* | 5/2013 | Komatireddy | ....... | A61B 5/0002 600/595 |

(Continued)

*Primary Examiner* — Sundhara M Ganesan
(74) *Attorney, Agent, or Firm* — Polsinelli PC

(57) ABSTRACT

Devices, systems, and methods for administering therapy to restore limb motion to patients in need are disclosed. The system may include a motion capture device to capture an exercise performed by a therapist. The exercise may be retrieved by the patient and used to generate a visual display used to guide the patient through the exercise in real time.

16 Claims, 23 Drawing Sheets

(51) Int. Cl.
*G16H 50/20* (2018.01)
*G16H 50/30* (2018.01)

(56) References Cited

U.S. PATENT DOCUMENTS

| | | | | |
|---|---|---|---|---|
| 2014/0081659 A1* | 3/2014 | Nawana | ................ | G16H 50/20 |
| | | | | 705/3 |
| 2014/0147820 A1* | 5/2014 | Snow | ................ | G06F 19/3481 |
| | | | | 434/247 |
| 2014/0153794 A1* | 6/2014 | Varaklis | ............... | A61B 5/1124 |
| | | | | 382/128 |
| 2014/0228985 A1* | 8/2014 | Elliott | ................... | A63B 71/06 |
| | | | | 700/91 |
| 2014/0287389 A1* | 9/2014 | Kallmann | ........... | G06F 19/3481 |
| | | | | 434/247 |
| 2014/0330408 A1* | 11/2014 | Rolley | ................ | G06F 19/3481 |
| | | | | 700/91 |
| 2014/0370470 A1* | 12/2014 | Aristizabal | ......... | G06F 19/3418 |
| | | | | 434/236 |
| 2015/0039106 A1* | 2/2015 | Bonstrom | ........... | G06F 19/3481 |
| | | | | 700/91 |
| 2015/0099252 A1* | 4/2015 | Anderson | ............ | G09B 19/003 |
| | | | | 434/257 |
| 2015/0213729 A1* | 7/2015 | Rhea | ................ | G06F 19/3481 |
| | | | | 434/247 |
| 2016/0008661 A1* | 1/2016 | Ferro Bento | ....... | G06F 19/3481 |
| | | | | 702/150 |

\* cited by examiner

DEVICES, SYSTEMS, AND METHODS FOR ADMINISTERING THERAPY

The present application claims the benefit under 35 U.S.C. § 119(e) of U.S. Provisional Patent Application No. 62/055,430, entitled "Devices, Systems, and Methods for Administering Therapy," filed on Sep. 25, 2014, which is incorporated herein by reference in its entirety.

TECHNICAL FIELD

The present disclosure relates to devices, systems, and methods for administering therapy to restore limb motion to patients in need.

BACKGROUND

For patients with chronic loss of limb motion, such as with stroke victims, it is essential to restore the brain functions linking desired and actual limb motions via physical therapy. This retraining of the brain may be accomplished by repetitions of fairly simple limb motions, typically under the guidance of a physical therapist or other practitioner. Typically, patients receive physical therapy from a physical therapist in person, wherein the physical therapist guides the patient through a series of limb movements or exercises designed to restore at least partial limb function. The therapist may guide the patient through each desired exercise by either physically manipulating the patient's limb, and/or providing feedback to the patient regarding the quality of the patient's movements during the exercise. The therapist may administer the physical therapy to the patient in the therapist's office or other facility, or the therapist may travel to the patient's home, hospital room, or other location to administer the physical therapy. This method of administering physical therapy may limit the amount of physical therapy available to the patient due to the limited availability of the therapist, the logistical challenge of traveling to a physical therapist's facility, and the expense of office visits and/or home visits with the therapist.

There exist at least several unique challenges associated with the administration of physical therapy to restore limb movement to patients with chronic loss of limb motion that are not typically addressed by existing systems. In order to administer physical therapy to restore limb movement to patients with chronic loss of limb motion, the desired motions associated with the therapy are typically customized by the therapist for each patient according to need. In addition, the capability of the patient to perform a desired limb motion may evolve from little or no capability to full capability over time, and the therapist typically monitors the patient's performance and modifies the prescribed motions to provide an appropriate match to the patient's current abilities. As a result, a home-based system may need to administer physical therapy exercises that are individually customized to each patient and designed to evolve over time as the patients capabilities evolve.

Further, the desired motions associated with the physical therapy may be very specific in that the posture of each portion of the limb during the motion is crucial to the effectiveness of the therapy. For example, a desired motion may entail laterally extending an arm in a prescribed plane of movement while maintaining the elbow and shoulder in a relatively fixed position to target specific muscle groups in need of development. In addition, many patients with chronic loss of limb motion may make use of external supports or braces to accomplish the desired limb motions, and/or may be confined to wheelchairs or beds. Typically, the therapist may physically manipulate the limb of the patient to ensure that the exercise is performed with proper limb posture and range of movement. A home-based system may need to provide the capability to provide specific and meaningful guidance to the patient regarding appropriate posture during a limb movement. In addition, the home-based system may further need to provide compatibility with patients wearing supports and/or braces, bed-ridden patients, and/or wheelchair-bound patients.

A need exists for a devices, systems, and methods of administering physical therapy to patients with chronic loss of limb motion. Such devices, systems, and methods may provide the ability for a patient to receive in-home therapy. This in-home therapy may be custom-designed by a therapist, may be monitored and/or scored to provide continuous assessment of the patient's progress, and the patient's progress may be communicated to the therapist and/or stored for subsequent analysis. The devices, systems, and methods may further provide the ability to record exercise demonstrations by the therapist and to incorporate the therapist's demonstrations and other instructions into the in-home therapy communicated to the patient.

BRIEF SUMMARY

The present disclosure is directed to devices, systems, and methods of administering physical therapy to patients with chronic loss of limb motion. As described herein, such devices, systems, and methods may provide the ability for a patient to receive in-home therapy.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

DETAILED DESCRIPTION

Figure 1:
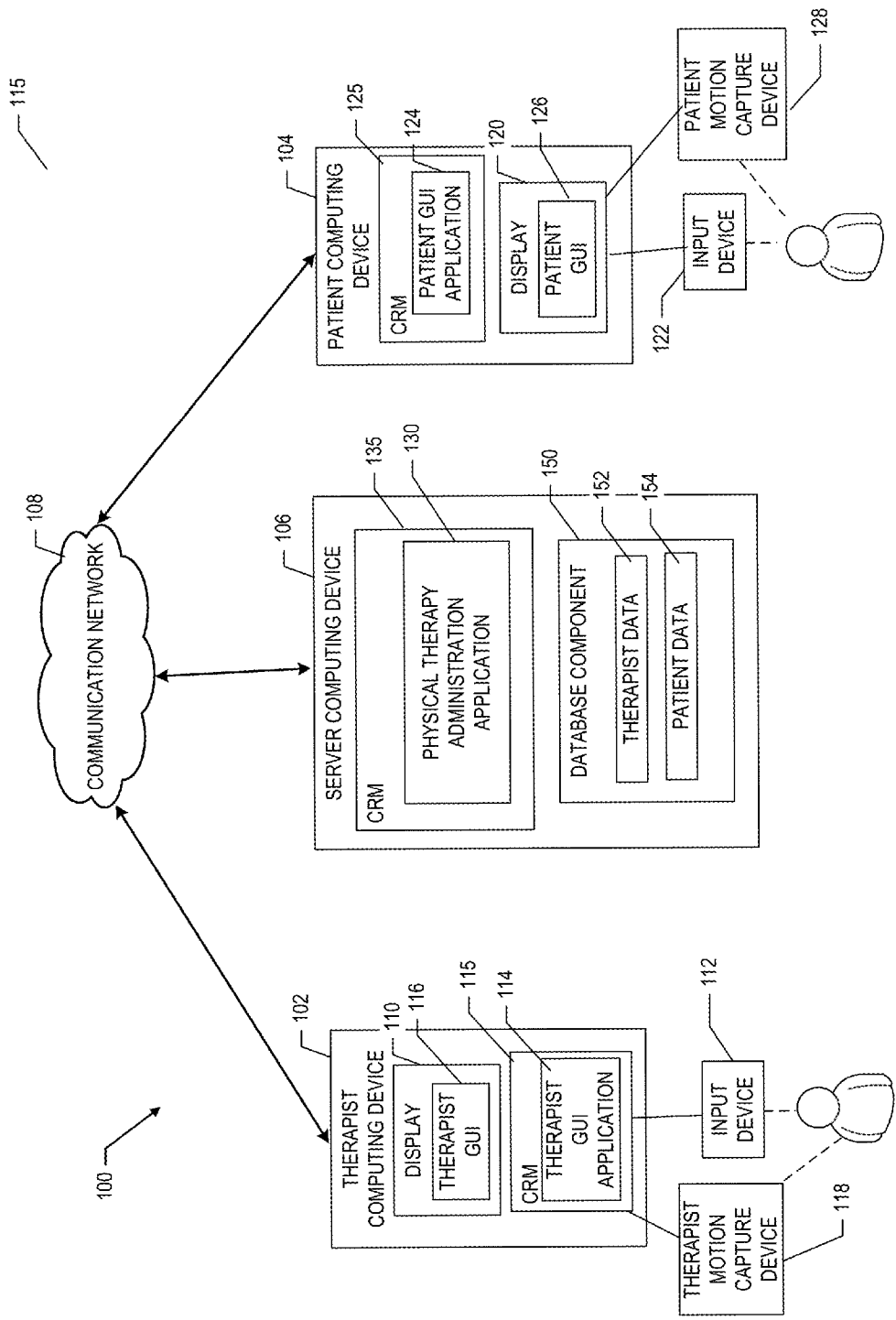
FIG. 1 is a block diagram of computing environments for remotely administering a physical therapy to a subject.

In various aspects, a physical therapy administration system (PTAS) is described herein that enables the remote administration of a physical therapy regime to a patient in need including, but not limited, to a patient exhibiting chronic loss of limb motion. The PTAS may enable a therapist to record and store at least one exercise that includes at least one desired limb motion to be performed by the patient as part of a physical therapy session. The PTAS further enables the therapist to assemble and store at least one physical therapy session record that may include one or more stored exercises, a desired number of repetitions for each exercise, the desired precision of the patient's movements for each exercise, as well as additional information including, but not limited to, the objectives of the physical therapy session and other communications to the patient from the therapist. The PTAS additionally enables the patient to retrieve at least one physical therapy session record stored by the therapist, perform at least one exercise while recording the patient's movements, and review the recorded movements and one or more scores assigned to the at least one exercise by the PTAS. The scores and recorded movements may be stored by the PTAS for subsequent review and analysis by the therapist.

In various other aspects, a brace is described herein that provides support and/or guidance to a patient performing at least one exercise as part of a physical therapy regime. The brace may include at least two or more segments joined end-to-end by a series of at least two adjustable hinges. A portion of the segments may be affixed to the patient such that each segment of the portion of segments is affixed to a portion of a patient's limb situated between two adjacent joints of that portion. In addition, the segments and hinges of the brace may be configured to translate and rotate within a range of motion that is comparable to the potential range of motion of the patient's limb. In an aspect, one or more of the adjustable hinges may be modified to reduce the range of motion of that hinge to a portion of the potential range of motion. In this aspect, the therapist may modify the range of motion of the patient's limb using the brace to guide the limb along a predetermined limb trajectory. This limb trajectory may be specified by the therapist in order target muscle groups associated with restored limb movement. In another aspect, the brace may further include additional instrumentation including, but not limited to an angle transducers, gyroscopes, and/or accelerometers to monitor the position of the patient's limb during a physical therapy session. In yet another aspect, the brace may also include one or more actuators to provide assistance in moving the patient's limb during a physical therapy session.

Detailed descriptions of the physical therapy administration system, the brace, and methods of using the physical therapy administration system and/or brace to design and administer a physical therapy regimen to a patient in need are described herein below in various aspects.

I. Physical Therapy Administration System

FIG. 1 depicts one embodiment of a PTAS system 100. The PTAS 100 may include a therapist computing device 102, a patient computing device 104, and a server computing device 106. The computing devices 02/104/106 may communicate via a communication network 108. The server 106 includes one or more processors and memory and is configured to receive data and/or communications from, and/or transmit data and/or communications to the therapist computing device 102 and the patient computing device 104 via the communication network 108.

The communication network 108 can be the Internet, an intranet, or another wired or wireless communication network. In this example, the therapist computing device 102, the patient computing device 104, and the server 106 may communicate data between one other using Hypertext Transfer Protocol (HTTP), a protocol commonly used on the Internet to exchange information between remote device computers and servers. In another aspect, the therapist computing device 102, the patient computing device 104, and the server 106 may exchange data via a wireless communication signal, such as using a Wireless Application Protocol (WAP), which is a protocol commonly used to provide Internet service to digital mobile phones and other wireless devices.

According to one aspect, the therapist computing device 102 may be a computing or processing device that includes one or more processors and memory and is configured to receive data and/or communications from, and/or transmit data and/or communications to the server 106 via the communication network 108. For example, the therapist computing device 102 may be a laptop computer, a personal digital assistant, a tablet computer, standard personal computer, or another processing device. The therapist computing device 102 may include a display 110, such as a computer monitor, for displaying data and/or graphical user interfaces. The therapist computing device 102 may further include an input device 112, such as a keyboard or a pointing device (e.g., a mouse, trackball, pen, or touch screen) to enter data into or interact with graphical user interfaces.

The therapist computing device 102 may also include a therapist graphical user interface (GUI) application 114 such as a browser application, to generate a therapist graphical user interface (GUI) 116 on the display 110; the therapist GUI application 114 may be stored on a computer readable medium (CRM) 115. The therapist GUI 116 enables the therapist to use the therapist computing device 102 to interact with data entry forms received from the server 106 to perform a variety of tasks associated with the administration of a physical therapy regime for a patient including, but not limited to: recording and storing exercises, assembling and storing physical therapy session records, and reviewing scores and recorded movements generated and stored by the patient using the PTAS 100 as described herein below.

The PTAS system 100 may further include a therapist motion capture device 118 in communication with the therapist communication device 102. The therapist motion capture device 118 may be used by the therapist to record a limb motion to provide an example of a desired limb motion to be performed by the patient as part of a physical therapy session. In various aspects, the therapist motion capture device 118 may include sensors to non-invasively obtain measurements used to record the limb motion including, but not limited to, one or more video cameras and/or one or more rangefinders or other distance sensors.

In one aspect, the therapist motion capture device 118 may be operated using a therapist motion capture module (not shown) operating on the therapist computing device 102 and/or the server 106. In this aspect, the therapist motion capture module may communicate with the therapist via the input device 112 and display 110 of the therapist computing device 102 to operate the therapist motion capture device 118. In another aspect, the therapist motion capture device 118 may include a separate and dedicated input device, display, processors and/or memory configured to communicate with the therapist and operate the therapist motion capture device 118. A more detailed description of suitable therapist motion capture devices 118 is provided herein below.

According to one aspect, the patient computing device 104 may be a computing or processing device that includes one or more processors and memory and is configured to receive data and/or communications from, and/or transmit data and/or communications to the server 106 via the communication network 108. For example, the patient computing device 104 may be a laptop computer, a personal digital assistant, a tablet computer, standard personal computer, or another processing device. The patient computing device 104 may include a display 120, such as a computer monitor, for displaying data and/or graphical user interfaces. The patient computing device 104 may further include an input device 122, such as a keyboard or a pointing device (e.g., a mouse, trackball, pen, or touch screen), to enter data into or interact with graphical user interfaces.

The patient computing device 104 may also include a patient graphical user interface (GUI) application 124, such as a browser application, to generate a patient graphical user interface (GUI) 126 on the display 120; the patient GUI application 124 may be stored on a computer readable medium (CRM) 125. The patient GUI 126 enables the patient to use the patient computing device 104 to interact with data entry forms received from the server 106 to perform a variety of tasks associated with the performance of a physical therapy regime from the therapist including, but not limited to, retrieving a stored physical therapy session record from the server 106, selecting and performing at least one exercise, and reviewing scores and/or recorded movements associated with a physical therapy session as described herein below.

The patient computing device 104 may further include a patient motion capture device 128 in communication with the patient computing device 104. The patient motion capture device 128 may be used by the patient to perform and record at least one limb motion associated with an exercise as part of a physical therapy session. In an aspect, the patient may be guided through the limb motion by at least one visual cue and/or auditory cue generated by the patient motion capture device 128 or display 120 of the patient computing device 104. The at least one visual cue and/or auditory cue may provide guidance to the patient with respect to the desired limb motion, and/or feedback to the patient regarding the accuracy of the patient's limb movement relative to the desired limb movement.

According to one aspect, the patient computing device 104 may be a computing or processing device that includes one or more processors and memory and is configured to receive data and/or communications from, and/or transmit data and/or communications to the server 106 via the communication network 108. For example, the patient computing device 104 may be a laptop computer, a personal digital assistant, a tablet computer, standard personal computer, or another processing device. The patient computing device 104 may include a display 120, such as a computer monitor, for displaying data and/or graphical user interfaces. The patient computing device 104 may further include an input device 122, such as a keyboard or a pointing device (e.g., a mouse, trackball, pen, or touch screen), to enter data into or interact with graphical user interfaces.

In one aspect, a visual cue may include a visual representation of the desired limb motion previously recorded by the therapist and retrieved from the server 106 as part of a stored therapy session record. One non-limiting example of a visual cue suitable for communicating a desired limb motion is an avatar that includes at least one animated limb moving along the desired limb trajectory. The visual cue may be generated by the display 120 of the patient computing device 104. In one aspect, the patient motion capture device 128 may further include a dedicated display (not shown) that may generate the visual cue. In another aspect, the patient motion capture device 128 may capture the limb motion of the patient and generate a visual cue and/or an auditory cue to indicate that the limb motion of the patient falls outside of a predetermined distance away from the desired limb motion. A more detailed description of the method of performance of an exercise by the patient using the patient computing device 104 and PTAS 100 is provided herein below.

In various aspects, the patient motion capture device 128 may further include sensors to non-invasively obtain measurements used to record the patient's limb motion including, but not limited to, one or more video cameras and/or one or more rangefinders or other distance sensors. In one aspect, the motion capture device 128 may be operated using a motion capture module (not shown) operating on the patient computing device 104 and/or the server 106. In this aspect, the patient motion capture module may communicate with the patient via the input device 122 and display 120 of the patient computing device 104 to operate the motion capture device 128. In another aspect, the motion capture device 128 may include a separate and dedicated input device, display, processors and/or memory configured to communicate with the patient and operate the motion capture device 128. A more detailed description of suitable motion capture devices 128 is provided herein below.

As illustrated in FIG. 1, the server 106 may further include a physical therapy administration application 130 stored on a CRM 135 and a database component 150. The physical therapy administration application 130 may include a plurality of modules executed by the one or more processors of the server 106 to enable the variety of tasks associated with the administration of the physical therapy regime as described herein. The database component 150 may include memory configured to store therapist data 152 and patient data 154. The therapist data 152 may include information used by the therapist to administer a physical therapy regimen including, but not limited to: patient medical records, recorded exercises used to develop physical therapy session records, and patient performance records used to assess the patient's limb mobility status. The patient data 154 may include information used by the patient to perform a physical therapy regimen including, but not limited to: physical therapy session records assigned to the patient by the therapist, and performance records used to provide feedback to the patient regarding the effectiveness of a physical therapy session. In various aspects, the therapist data 152 may be accessed only by the therapist and other authorized practitioners, and may contain information associated with more than one patient. In various other aspects, the patient data 154 may be accessed by the therapist and the patient, and typically contains information associated with that particular patient only.

Each computing device 102/104/106 typically includes at least one form of computer readable media 115/125/135. Computer readable media 115/125/135, which may include both volatile and nonvolatile media and/or removable and non-removable media, can be any available medium that may be accessed by a general purpose computing device. By way of example and not limitation, computer readable media 115/125/135 may include computer storage media and communication media. Computer readable media 142 may further include volatile and nonvolatile and/or removable and non-removable media implemented in any method or technology for storage of information such as computer readable instructions, data structures, program modules or other data. Communication media may typically embody computer readable instructions, data structures, program modules, or other data in a modulated data signal, such as a carrier wave or other transport mechanism and include any information delivery media. Those skilled in the art will be familiar with the modulated data signal, which may have one or more of characteristics set or changed in such a manner that permits information to be encoded in the signal.

Each computing device 102/104/106 may include or be capable of accessing computer storage media in the form of removable and/or non-removable and/or volatile and/or non-volatile memory. A user may enter commands and information into the computing device 102/104/106 through an input device. Other input devices (not shown) may also be connected to the computing device 102/104/106. Each computing device 102/104/106 may also operate in a networked environment using logical connections to one or more remote computers.

Figure 2:
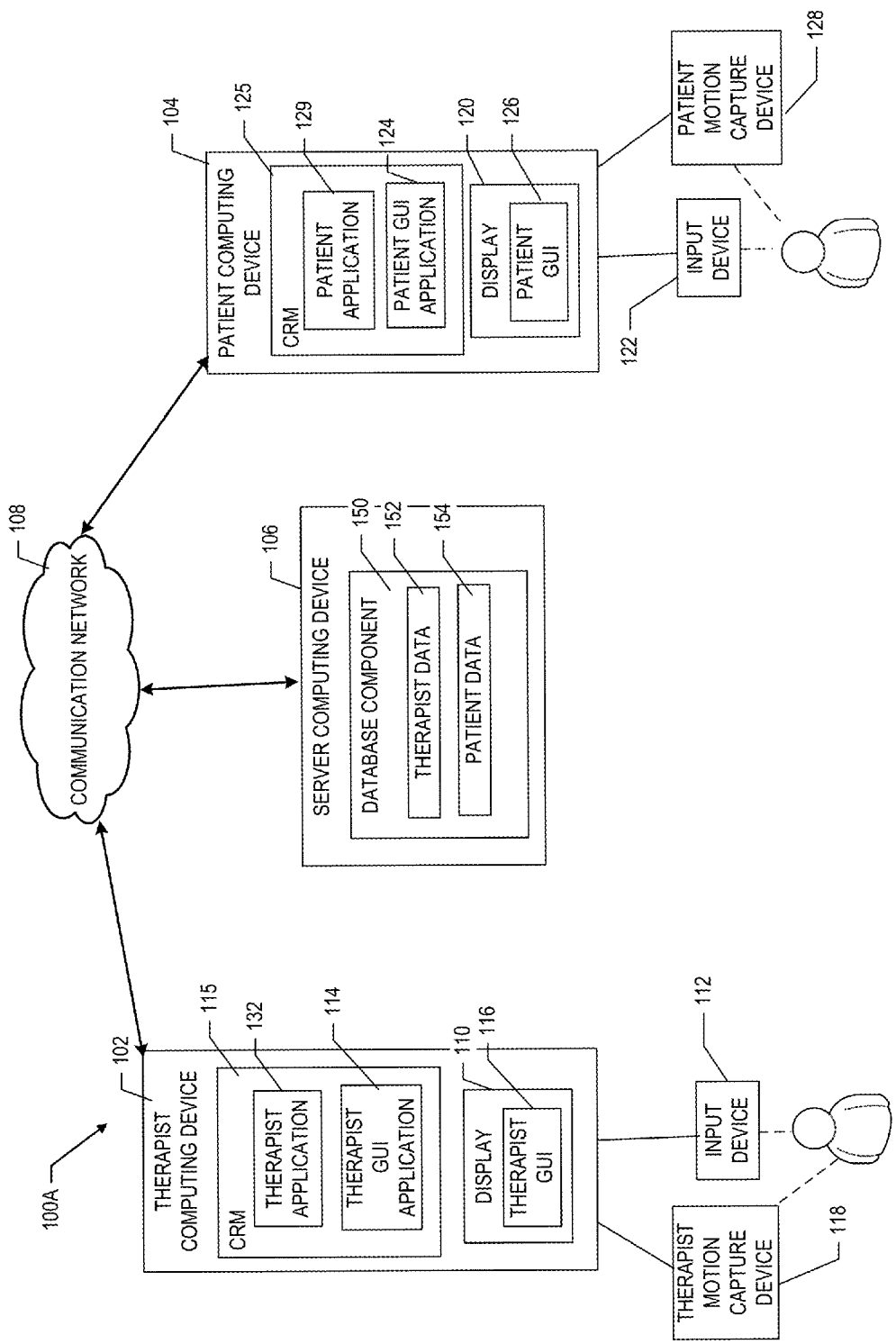
FIG. 2 is a block diagram of computing environments for remotely administering a physical therapy to a subject.

In various other aspects, the elements and devices of the PTAS 100 may be arranged in configurations which differ from the arrangement illustrated in FIG. 1. Referring to FIG. 2, in another aspect of the PTAS 100A, the therapist computing device 102 may further include a therapist application 132 and the therapist GUI application 114 stored on the CRM 115. In this other aspect, the patient computing device 104 may further include a patient application 136 and the patient GUI application 124 stored on the CRM 115. The therapist application 132 includes at least a portion of the plurality of modules of the physical therapy administration application 130 that enables the tasks performed by the therapist including, but not limited to, recording exercises and assembling instructions and data associated with a physical therapy session to be performed by the patient. The patient application 129 includes at least a portion of the plurality of modules of the physical therapy administration application 130 that enables the tasks performed by the patient including, but not limited to, performing, recording, and evaluating the patient's movements in response to the exercises recorded by the therapist.

Figure 3:
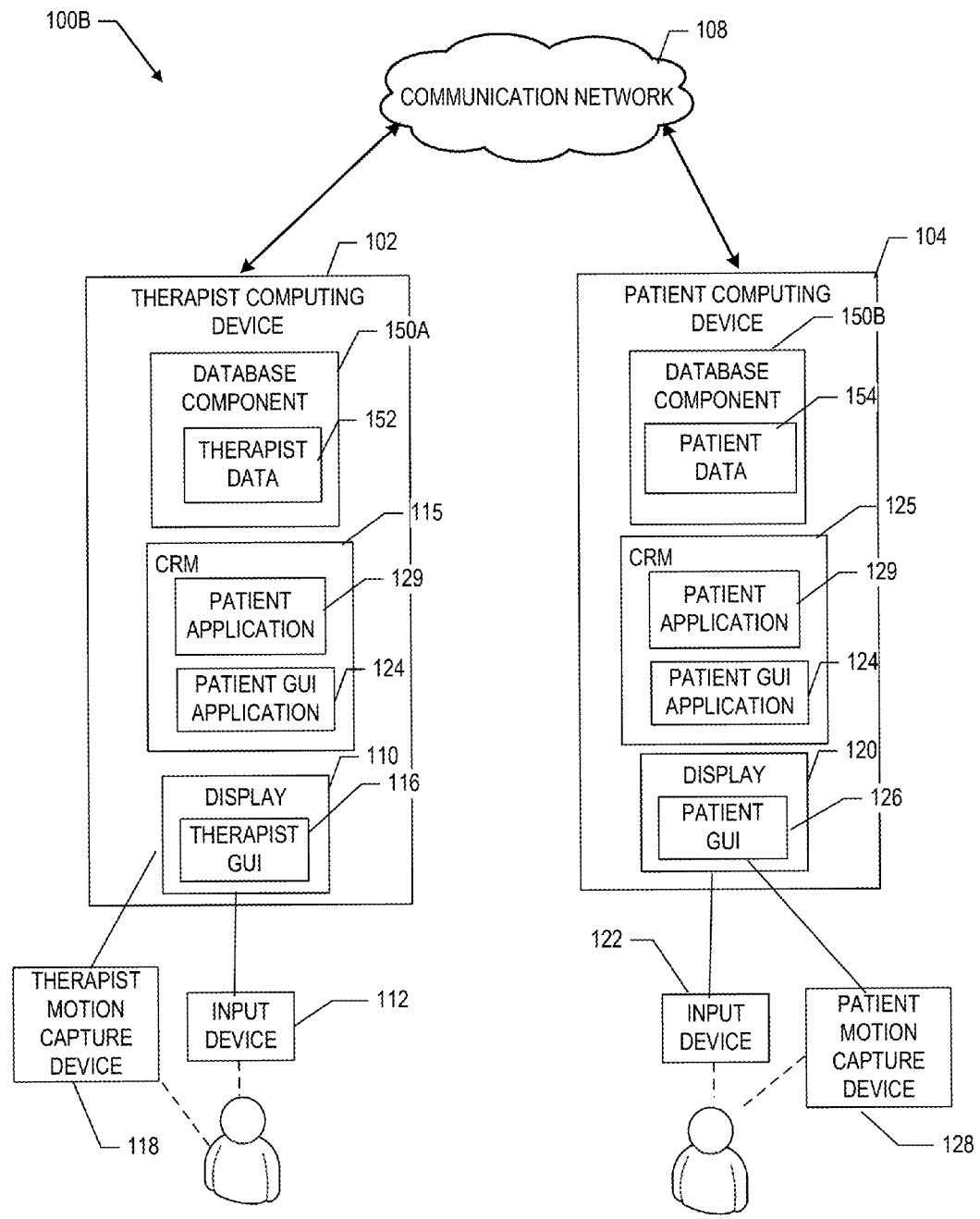
FIG. 3 is a block diagram of computing environments for remotely administering a physical therapy to a subject.

In an additional aspect, illustrated in FIG. 3, the PTAS 100B may include the therapist computing device 102 and the patient computing device 104 communicating via the communication network 108. In this additional aspect, the therapist computing device 102 may store the therapist data 152 locally on a database component 150A provided within the therapist computing device 102. Further, the patient computing device 104 may store the patient data 154 locally on a database component 150B provided within the patient computing device 104.

Figure 4:
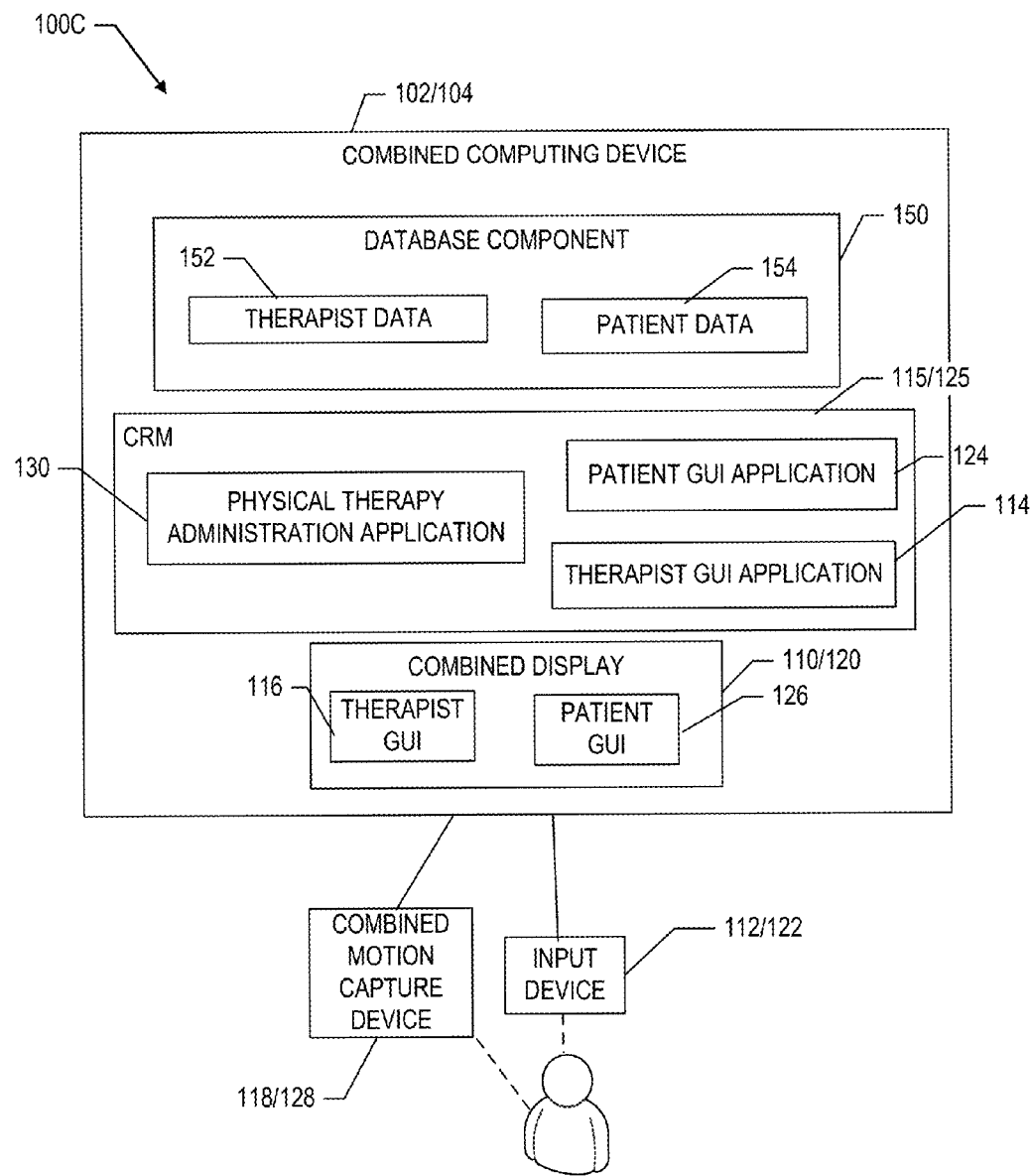
FIG. 4 is a block diagram of computing environments for remotely administering a physical therapy to a subject.

In yet another aspect, illustrated in FIG. 4, the PTAS 100C may include a combined computing device 102/104 to be used by both the therapist and the patient. In this additional aspect, the combined computing device 102/104 may store the therapist data 152 and the patient data 154 within a combined database component 150. The combined computing device 102/104 may further include a CRM 115/125 encoded with the physical therapy administration application 130, the therapist GUI application 114 and the patient GUI application 124. Further, the combined computing device 102/104 may include a combined display 110/120 that displays at least one therapist GUI 116 during use by the therapist and at least one patient GUI 126 during use by the patient. In this other aspect, a combined input device 112/122 may be used by both the therapist and the patient to enter commands and data associated with the administration of a physical therapy regime using the PTAS 100B. A combined motion capture device 118/128 may be used by the therapist to record exercises and by the patient to record the patient's movements in response to the recorded exercise(s) received from the therapist.

A. Physical Therapy Administration Module

Figure 5:
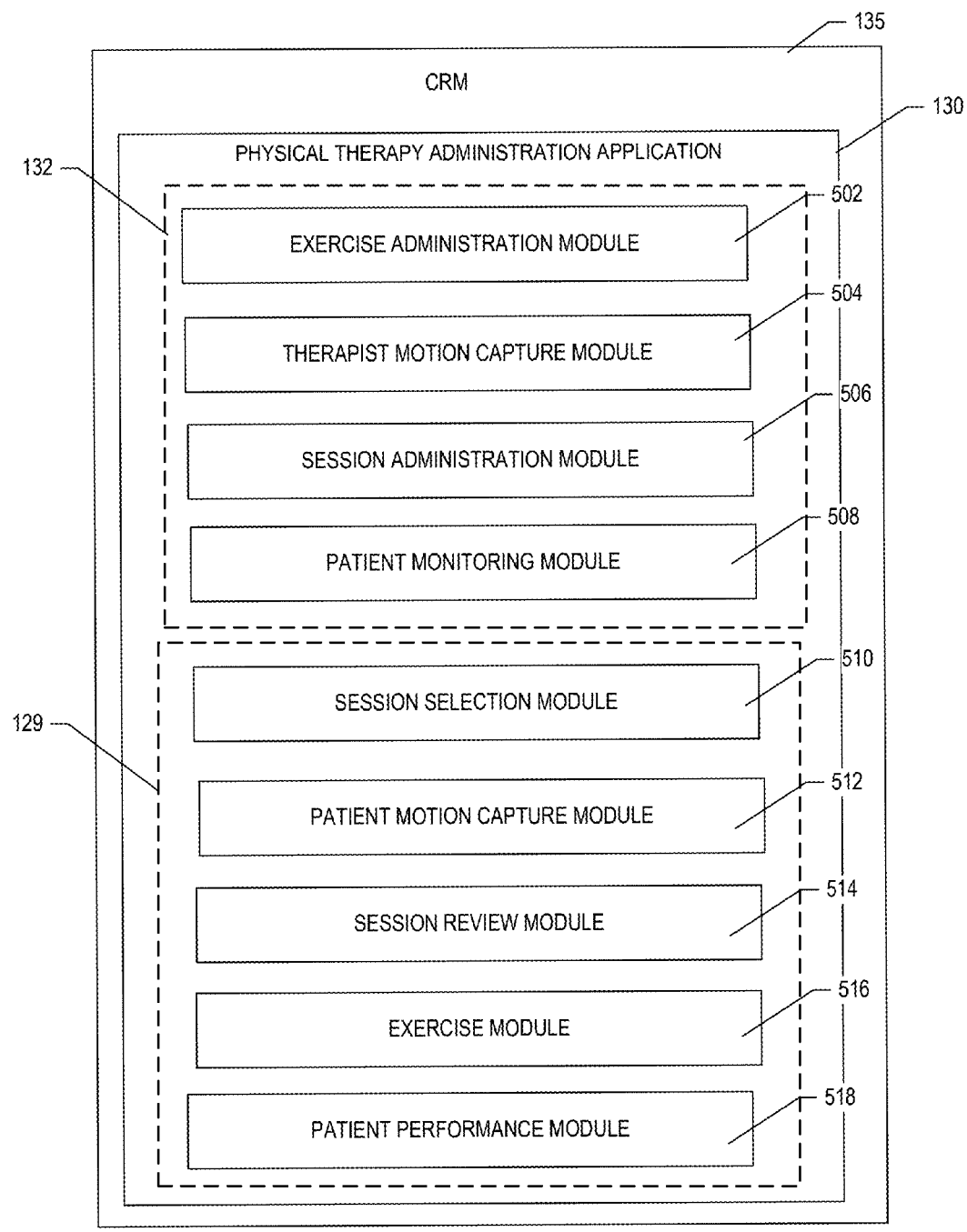
FIG. 5 is a block diagram showing the modules of a physical therapy administration application.

In various aspects, the physical therapy administration system 100 includes a physical therapy administration application 130, as illustrated in FIG. 4. FIG. 5 is a block diagram illustrating the modules of the physical therapy administration application 130 in various aspects. A portion of the modules of the physical therapy administration application 130, grouped as the therapist application 132 (see FIG. 2), enable the therapist to remotely administer a physical therapy regimen to a patient by recording exercises to be used as examples of a limb movements appropriate for a physical therapy session, assembling and transferring instructions for a physical therapy session to the patient, and monitoring the performance of the patient during the exercises of each physical therapy session of the physical therapy regime. Another portion of the modules of the physical therapy administration application 130, grouped as the patient application 129 (see FIG. 2), enable the patient to remotely perform a physical therapy regimen under the supervision of a therapist by selecting exercises previously recorded and selected by the therapist as appropriate for the patient's condition, performing the exercises and recording the patient movements as the response to the exercise, scoring at least one patient response according to at least one scoring rule, and providing the therapist and the patient with feedback regarding the patient's ability to perform the at least one exercise.

Exercise Administration Module

Figure 6:
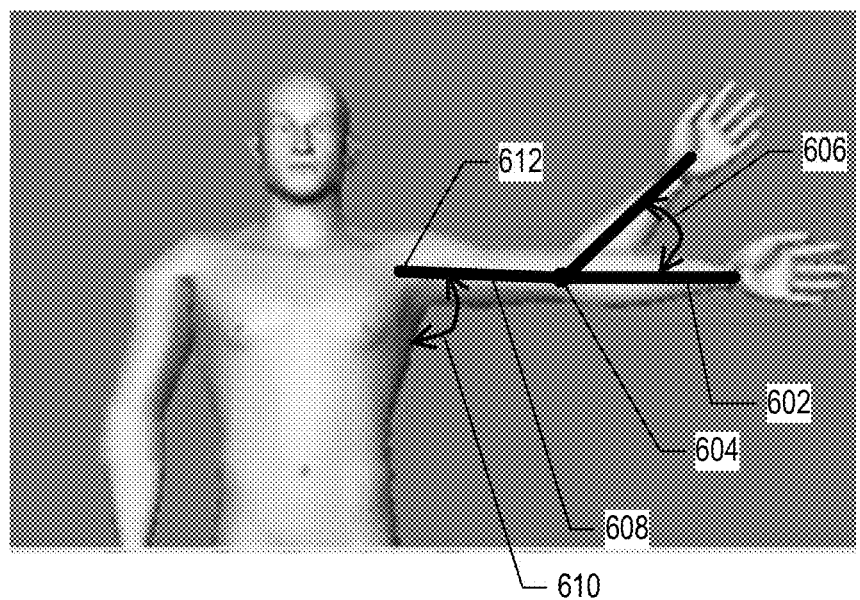
FIG. 6 is a schematic diagram illustrating various limb landmarks used to quantify a limb motion.

Referring again to FIG. 5, the physical therapy administration application 130 may include an exercise administration module 502. In various aspects, the exercise administration module 502 may enable the therapist to record at least one exercise associated with a physical therapy regime. An exercise, as referred to herein, refers to a limb movement associated with the physical therapy and typically entails a specific movement pathway configured to target one or more specific muscle groups in need of strengthening or enhanced activation. Referring to FIG. 6, an exercise may include flexing and/or extending the forearm 602 at the elbow 604 through an angular range 606, while maintaining the angle 610 of the upper arm 608 at the shoulder 612 at a relatively constant angle. In this example, other aspects of the exercise, in addition to the limb movement, may include: the number of repetitions, the speed at which the limb is moved, and the allowable movement of other parts of the patient's body, such as the allowable changes in the shoulder angle 610.

Figure 7:
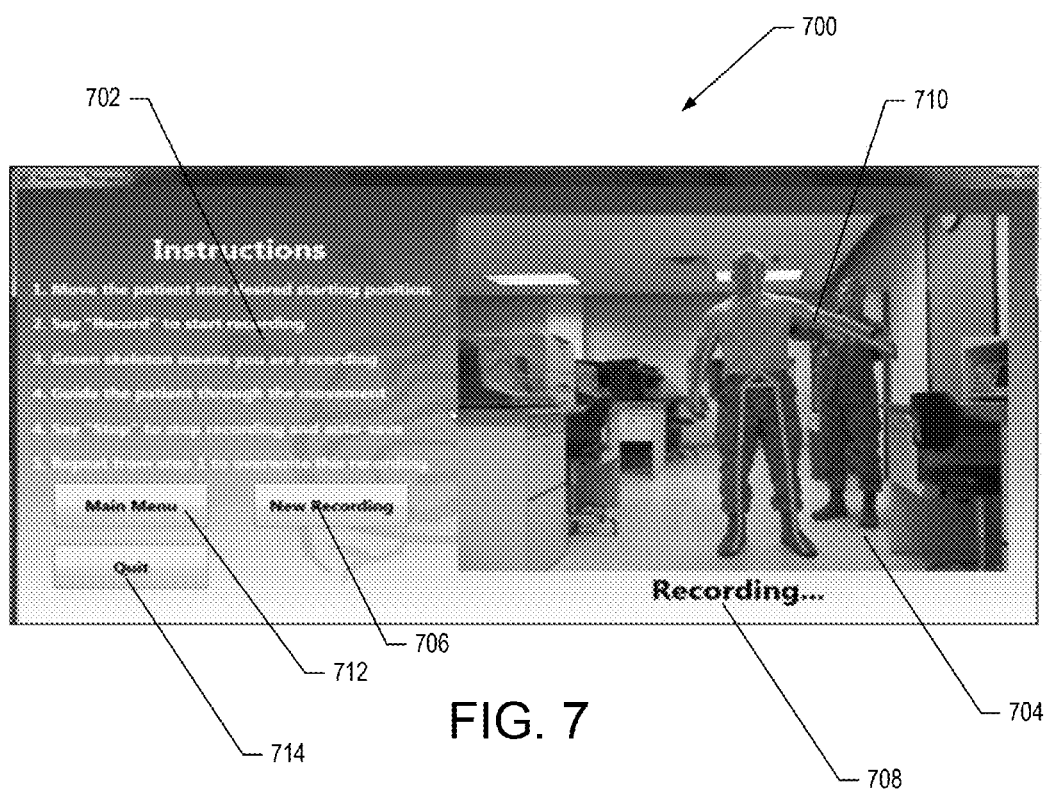
FIG. 7 is a screen shot of an exercise recording form during the recording of an exercise.

The exercise administration module 502 may display forms generated by the therapist GUI application 114 to enable the recording of an exercise. FIG. 7 depicts an exercise recording form 700 that enables the therapist to record an exercise for use as a visual aid to a patient performing the exercise as part of a physical therapy session. The exercise recording form 700 may include a list of instructions 702 to aid the therapist in performing the steps needed to record an exercise. The exercise recording form 700 may further include a video window 704 displaying the view of the camera used to capture the exercise motion. The information represented in the video window enables the therapist to position the patient and/or therapist at an appropriate distance away from the camera and ensure that sufficient light and subject contrast is provided. By selecting the "new recording control" 706 the therapist may initiate the recording of a new exercise. The exercise administration module 502 may activate the therapist motion capture module 504, thereby enabling the operation of the therapist motion capture device 118. By way of non-limiting example, the therapist motion capture device 118 may use voice commands to start and stop the camera from recording. The exercise recording form 700 may provide additional indications that recording is active, including a text message 708 or a color coding such as a green color assigned to the digitized limb segments 710 as illustrated in FIG. 7. In addition, the current recording may be overwritten according to the exercise recording form 700 illustrated in FIG. 7 by simply stopping and restarting the recording camera.

Figure 8:
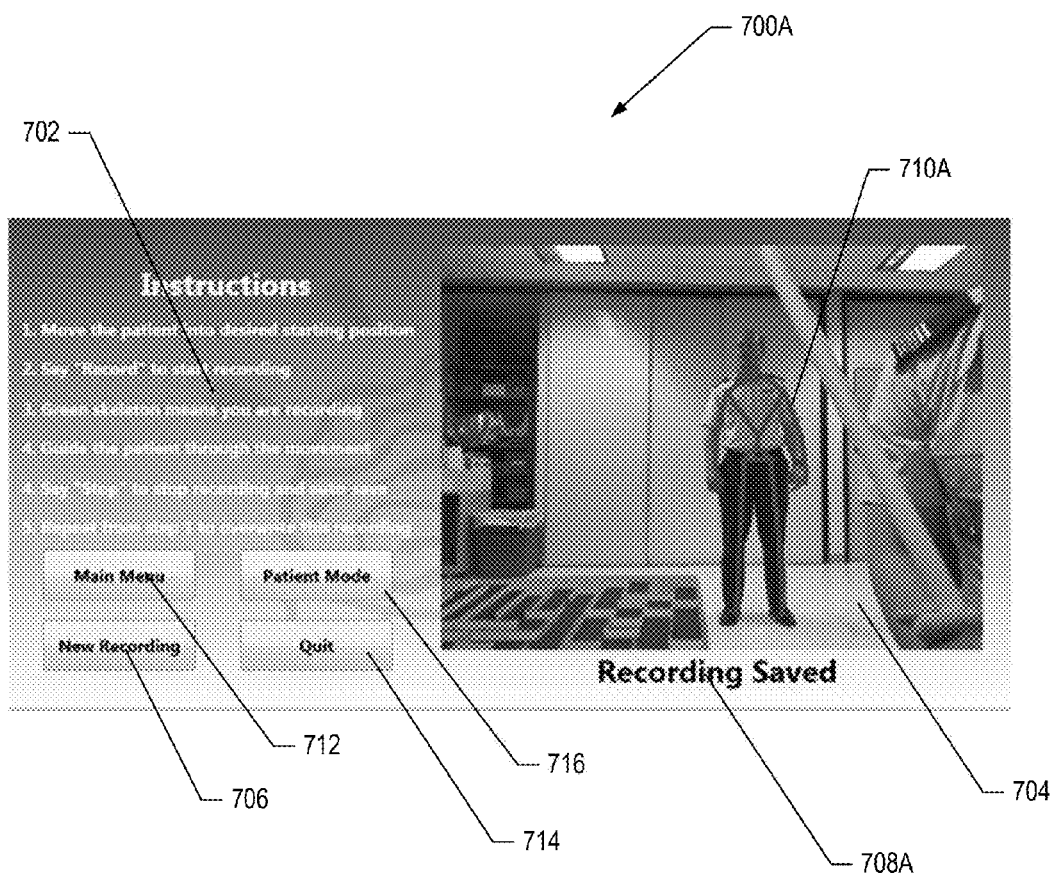
FIG. 8 is a screen shot of an exercise recording form after the recording of an exercise.

As each recording is stopped, the captured motion may be saved and a modified exercise recording form 700A may be displayed, as illustrated in FIG. 8. The modified exercise recording form 700A may provide additional indications that recording has stopped, including the text message 708A or a color coding including, but not limited to, the color red assigned to the digitized limb segments, as illustrated in FIG. 8. The therapist may select the "new recording" control 706 to restart recording a motion without overwriting the previously-saved exercise in an aspect. In another aspect, the therapist may select the "main menu" control to return to a main screen form (not shown) for further use of the physical therapy administration system 100. In an additional aspect, the "quit" control 714 may be selected to exit the physical therapy administration application 130. In an additional aspect, the "patient mode" control 716 may be selected to use the same motion capture device to record an exercise and to administer an exercise to the patient as part of a physical therapy regimen using the combined system 100C illustrated in FIG. 4.

In other aspects, the exercise administration module 502 may enable the therapist to perform additional manipulations of the exercise captured by the therapist motion capture device. Non-limiting examples of additional manipulations include: reviewing the captured motion; modifying the captured motion by cropping out undesired frames, and manipulating the brightness or contrast of the captured motion video record, and the like.

Therapist Motion Capture Module

Referring again to FIG. 5, the physical therapy administration application 130 may include a therapist motion capture module 504 in various aspects. The therapist motion capture module 504 may act as an interface between the therapist motion capture device 118 and the physical therapy administration system 100. For example, as described herein previously, the GUI forms may be used to transmit specific commands to the elements of the therapist motion capture device 118. Suitable specific commands to the therapist motion capture device 118 include: start motion capture, stop motion capture, clear previous motion capture, save previous motion capture, modulate camera setting such as exposure, focus, zoom, and the like; calibrate the therapist motion capture device 118; and calibrating the camera placement or field of view of the cameras prior to capturing motion.

Session Administration Module

Referring again to FIG. 5, the physical therapy administration application 130 may include a session administration module 506 in various aspects. The session administration module 506 may enable the therapist to assemble a physical therapy session for one or more patients as part of each patient's physical therapy regimen. In one aspect, the session administration module 506 may enable the therapist to select one or more stored exercises to include in a physical therapy session for a patient. In another aspect, the therapist may add additional information to the exercises selected for a physical therapy session including, but not limited to: number of repetitions of each exercise, the speed at which each exercise should be performed, the objective of each exercise, and/or the physical therapy session. In another additional aspect, the session administration module 506 may enable the therapist to store the physical therapy session data in the therapist data 152 and or in the patient data 154 indexed to associate each physical therapy session data with an individual patient.

Patient Monitoring Module

Referring again to FIG. 5, the physical therapy administration application 130 may include a patient monitoring module 508 in various aspects. The patient monitoring module 508 may enable the therapist to review one or more records from the database component 150. Non-limiting examples of records that may be reviewed by the therapist include one or more of a patient's response to a physical therapy session including, but not limited to: the patient's limb motion compared to the desired limb motion, one or more scores generated by the patient performance module 518, patient medical records, and therapist notes for the patient. In an aspect, the patient monitoring module 508 may enable the therapist to enter additional data and notes including, but not limited to: recommendations for subsequent physical therapy sessions, notes on patient progress and prognosis, and any other relevant information.

Session Selection Module

The physical therapy administration application 130 may include a session selection module 510 in various aspects. The session selection module 510 may enable the patient to review and select a physical therapy session assembled by the therapist using the session administration module 506 and stored in a patient-accessible portion of the of the database component 150. In various aspects, the patient may use the session selection module 510 to repeat a previous physical therapy session to enhance the benefits of the session. In various other aspects, the patient may use the session selection module 510 to alternate between two or more physical therapy sessions to enrich the variety of exercises available to the patient and/or to provide opportunity to alternate work and rest periods for elected muscle groups targeted by the two or more physical therapy sessions. In another aspect, the patient may select an individual exercise using the session selection module 510.

Figure 11:
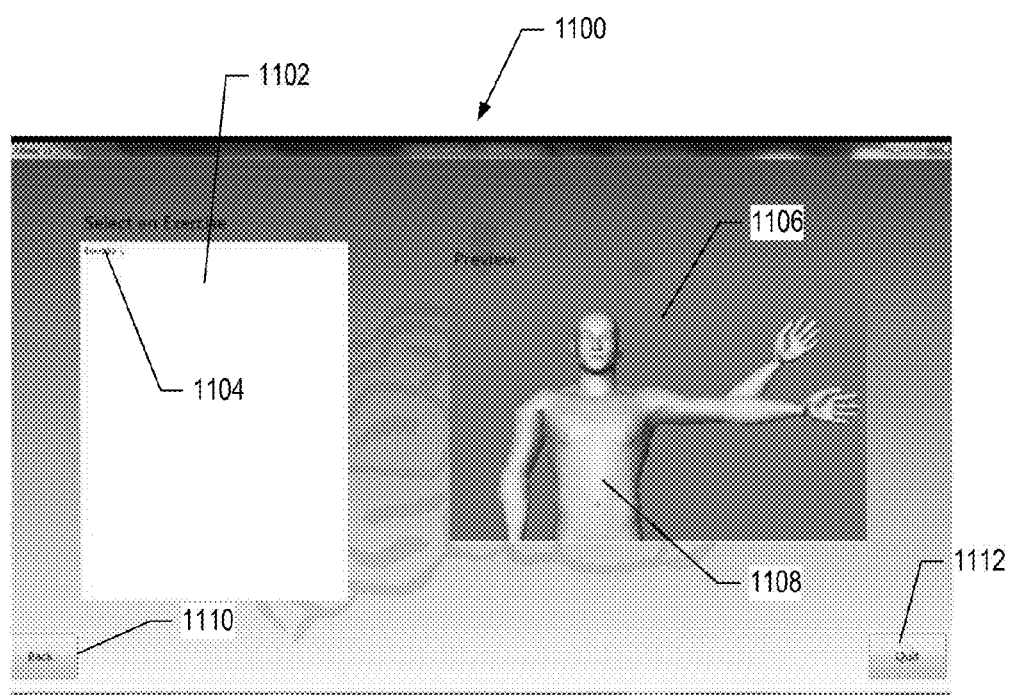
FIG. 11 is a screen shot of an exercise selection form.

The session selection module 510 may display forms generated by the patient GUI application 124 to enable the selection of a session and/or exercise to be performed by the patient. FIG. 11 depicts an exercise selection form 1100 that enables the patient to review performance during one or more exercises. As illustrated in FIG. 11, the exercise selection form 1100 includes an exercise menu window 1102 listing one or more entries 1104 listing each available exercise that the patient may choose to perform. The exercise selection form 1100 includes an exercise menu window 1102, and may further include an exercise preview window 1106 containing a graphical representation 1108 of the exercise currently selected in the exercise menu window 1102. The exercise selection form 1100 may further include one or more controls including, but not limited to, a "back" control 1110 and a "quit" control 1112. Selection of an exercise entry 1104 within the exercise menu window 1102 initiates the exercise module 516 for the selected exercise.

Session Review Module

In another aspect, the physical therapy administration application 130 may include a session review module 512. In various aspects, the session review module 512 may enable the patient to review a performance during one or more previously completed physical therapy sessions. In one aspect, the patient may review the patient's response to one or more exercises included in a physical therapy session by reviewing the therapist-generated target limb trajectory provided in comparison to the movement achieved by the patient. The comparison between the target limb trajectory and the patient response may be provided in the form of graphs summarizing the spatial locations of various limb landmarks during a limb trajectory including, but not limited to: a graph including a target trajectory of a limb landmark and the corresponding patient trajectory of the same limb landmark; a graph of the differential displacement of the patient trajectory and target trajectory of the same limb landmark; a graph of a target trajectory and a patient trajectory of a common limb angle; and a graph of the difference in limb angles of the patient relative to the limb angles during the target limb trajectory. A limb landmark, as used herein, refers to any feature of a patient detectable by a motion capture device including, but not limited to: any joint including a shoulder, an elbow, an wrist, an ankle, a knee, or a hip; or a distal portion including a head, a hand, a foot, a finger, or a toe. In other aspects, the comparison between the target limb trajectory and the patient response may be provided in the form of one or more scores generated by the patient performance module 518.

Figure 9A:
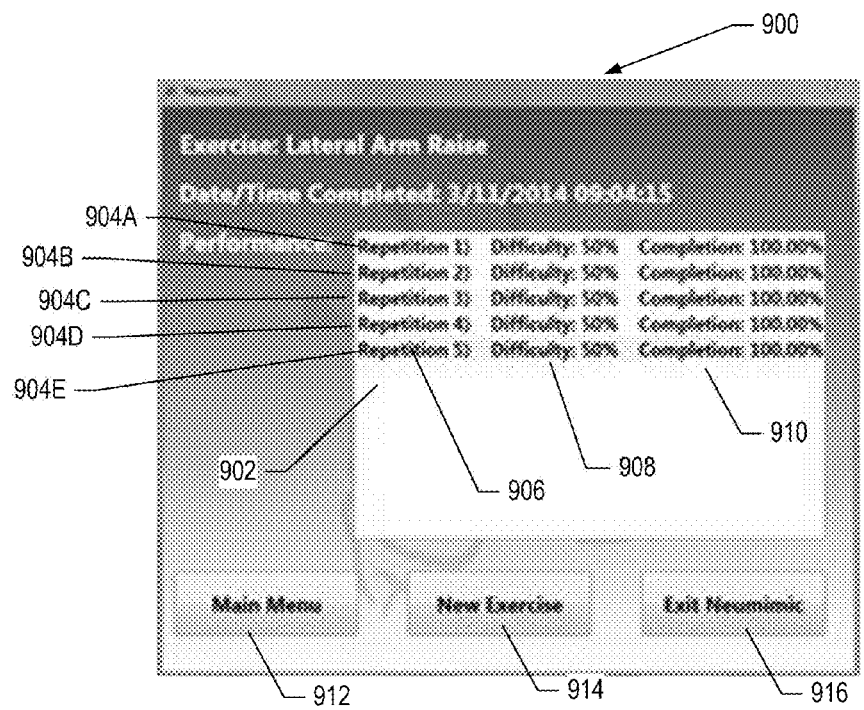
FIG. 9A is a screen shot of an exercise review form with a performance reporting window.
Figure 9B:
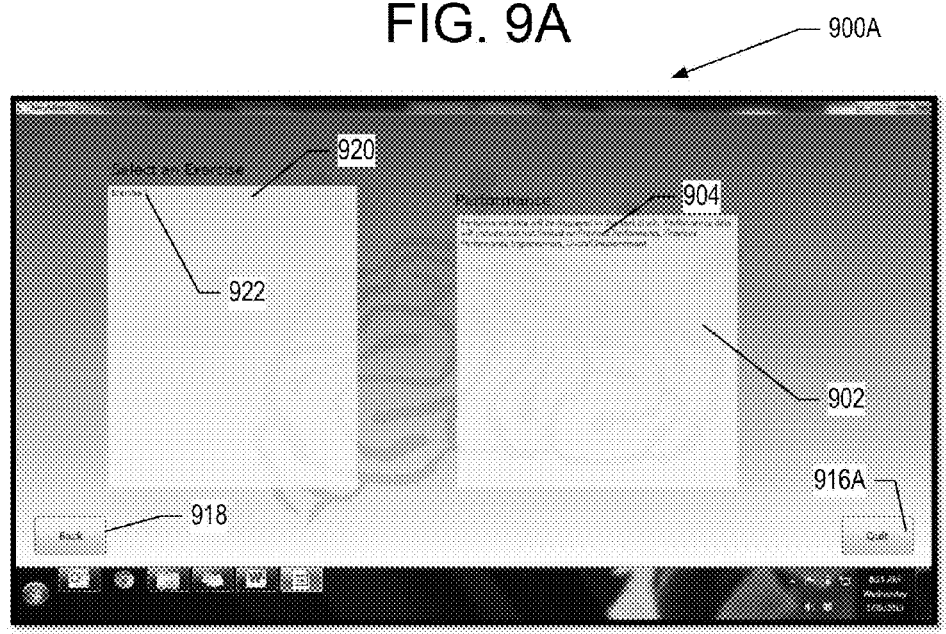
FIG. 9B is a screen shot of an exercise review form with an exercise menu window and a performance reporting window.
Figure 10:
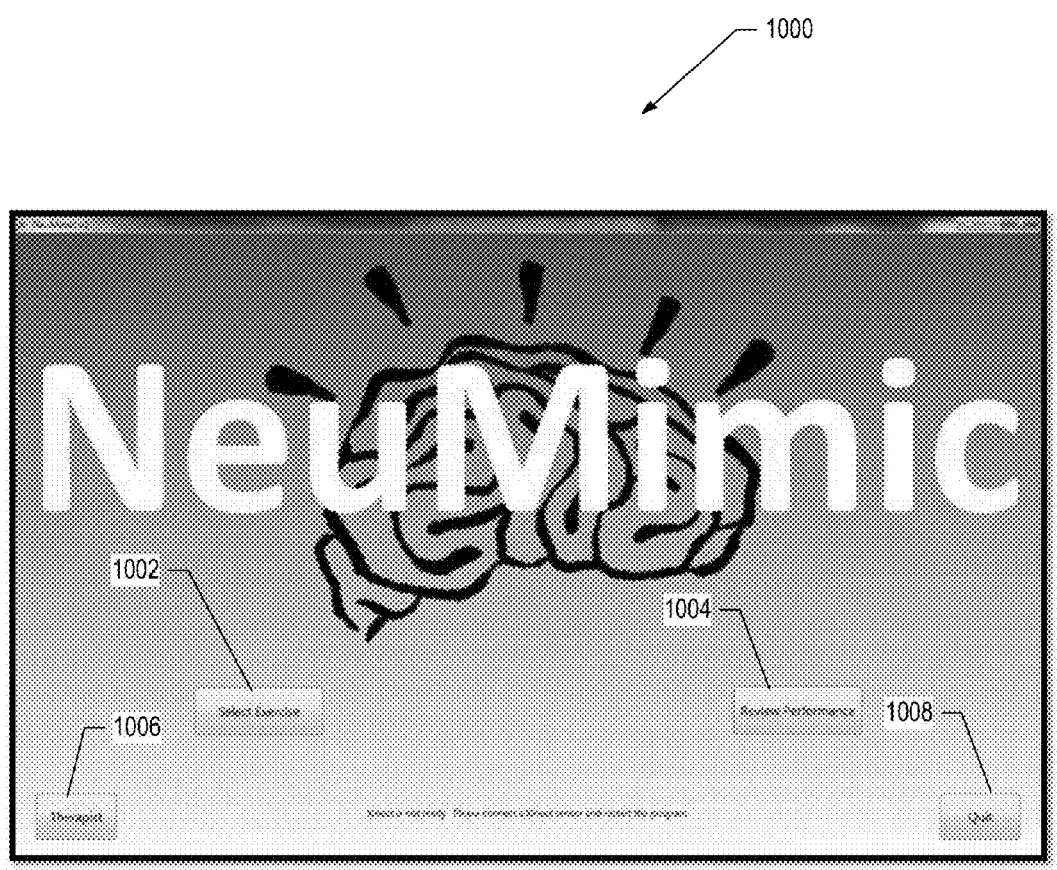
FIG. 10 is a screen shot of a main patient menu form.

The session review module 512 may display forms generated by the patient GUI application 124 to enable the review of the patient's response to one or more exercises selected during one or more previous physical therapy sessions. FIGS. 9A-9B depict an exercise review form 900/900A that enables the patient to review performance during one or more exercises. As illustrated in FIG. 9A, the exercise review form 900 includes a performance reporting window 902 list one or more entries 904A-904E to report the patient's performance on individual repetitions of an exercise. Each entry may contain several values associated with the patient's performance on an exercise as illustrated in FIG. 9 including, but not limited to: repetition number 906, difficulty level of repetition 908, and % of the exercise completed 910, as calculated by the patient performance module 518. In addition to the reporting window 902, the exercise review form 900 may further contain additional information about one or more previously-completed exercises including, but not limited to, name of exercise 912 and the date and time of completion of the exercise 914. The exercise review form 900 may further include a plurality of controls that may be selected by the patient to navigate among different parts of the physical therapy administration application 130. Selecting the "main menu" control 912 transfers the patient back to a main patient menu form 1000, as illustrated in FIG. 10.

As illustrated in FIG. 9B, the exercise review form 900A may further include an exercise selection menu 920 containing a list of entries 922 corresponding to exercises previously completed by the patient. In this aspect, the exercise review form 900A includes a performance reporting window 902 that lists the patient's performance during completion of the exercise entry 922 highlighted in the exercise selection menu 920.

Exercise Module

In another aspect, the physical therapy administration application 130 may include an exercise module 516 as illustrated in FIG. 5. In various aspects, the exercise module 516 may enable the patient to perform an exercise as part of a physical therapy session. In one aspect, the exercise module 516 may generate a visual display to provide the patient with a target limb movement in the form of a visual model of the desired limb movement of the exercise. In addition, the exercise module 516 may further capture the motion of one or more limb landmarks of the patient during an exercise using the patient motion capture device 128 and may compare each movement of a patient's limb landmark, such as an elbow, to the target movements of the corresponding limb landmark. The exercise module may further provide the patient with feedback including, but not limited to, a visual feedback or an auditory feedback to signal to the patient that the motion of the patient's limb has deviated outside of a threshold error relative to the target limb motion. A limb landmark, as used herein, refers to any feature of a patient detectable by a motion capture device including, but not limited to: any joint including a shoulder, an elbow, an wrist, an ankle, a knee, or a hip; or a distal portion including a head, a hand, a foot, a finger, or a toe.

In various aspects, the exercise module 516 may display forms generated by the patient GUI application 124 to enable the patient to perform one or more exercises associated with a physical therapy session. FIG. 12 depicts an exercise form 1200 in an aspect. The exercise form 1200 includes a video window 1202 displaying the view from a camera associated with the patient motion capture device 128. Superimposed in the video window is a visual representation 1204 of the target limb trajectory for the exercise. The target trajectory 1204 was previously recorded by the therapist using the therapist motion capture device 118 via the exercise administration module 502 and selected by the patient via the session selection module 510.

Figure 12A:
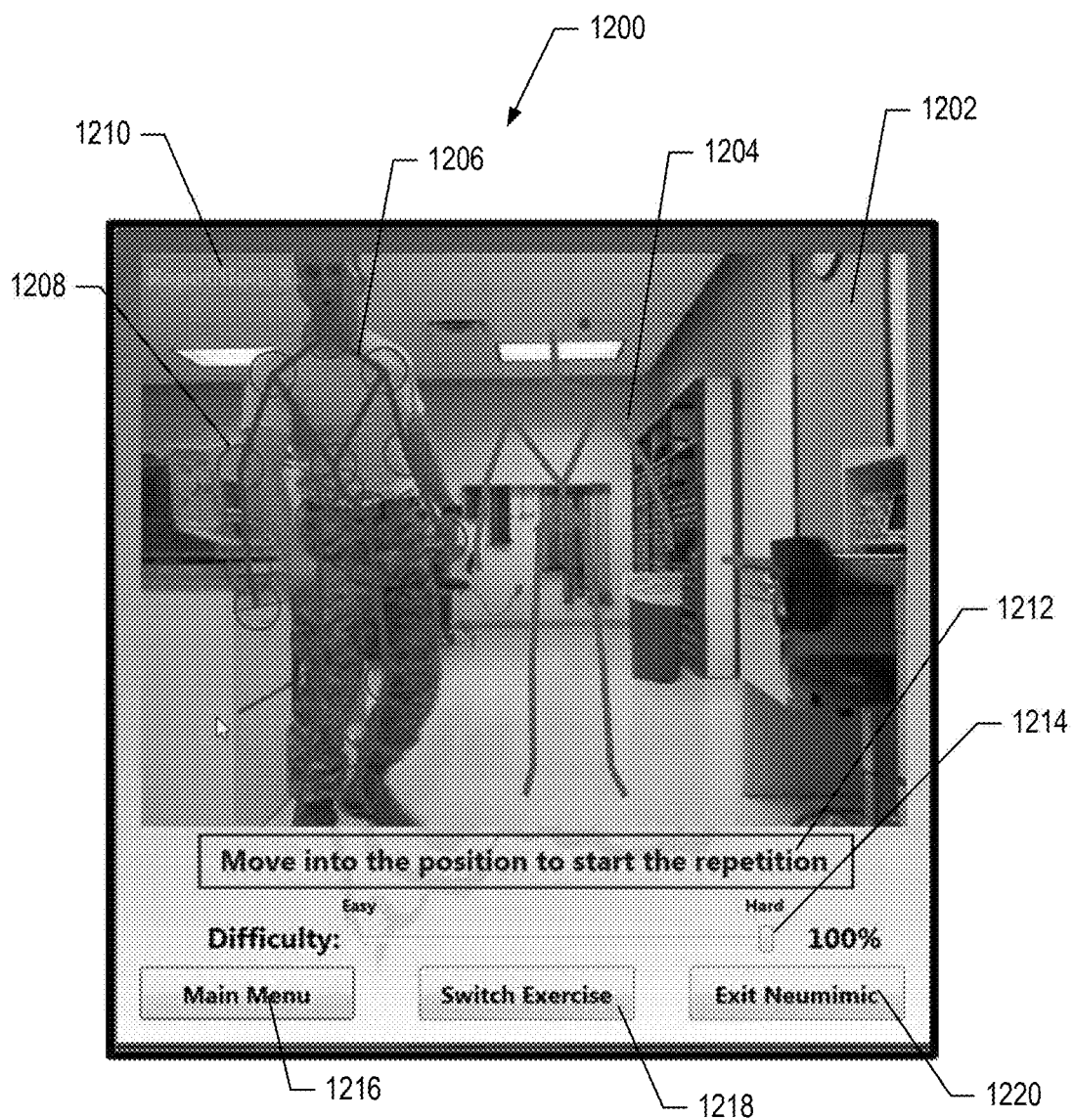
FIG. 12A is a screen shot of an exercise form with a misalignment between the patient limb trajectory and the target limb trajectory.
Figure 12B:
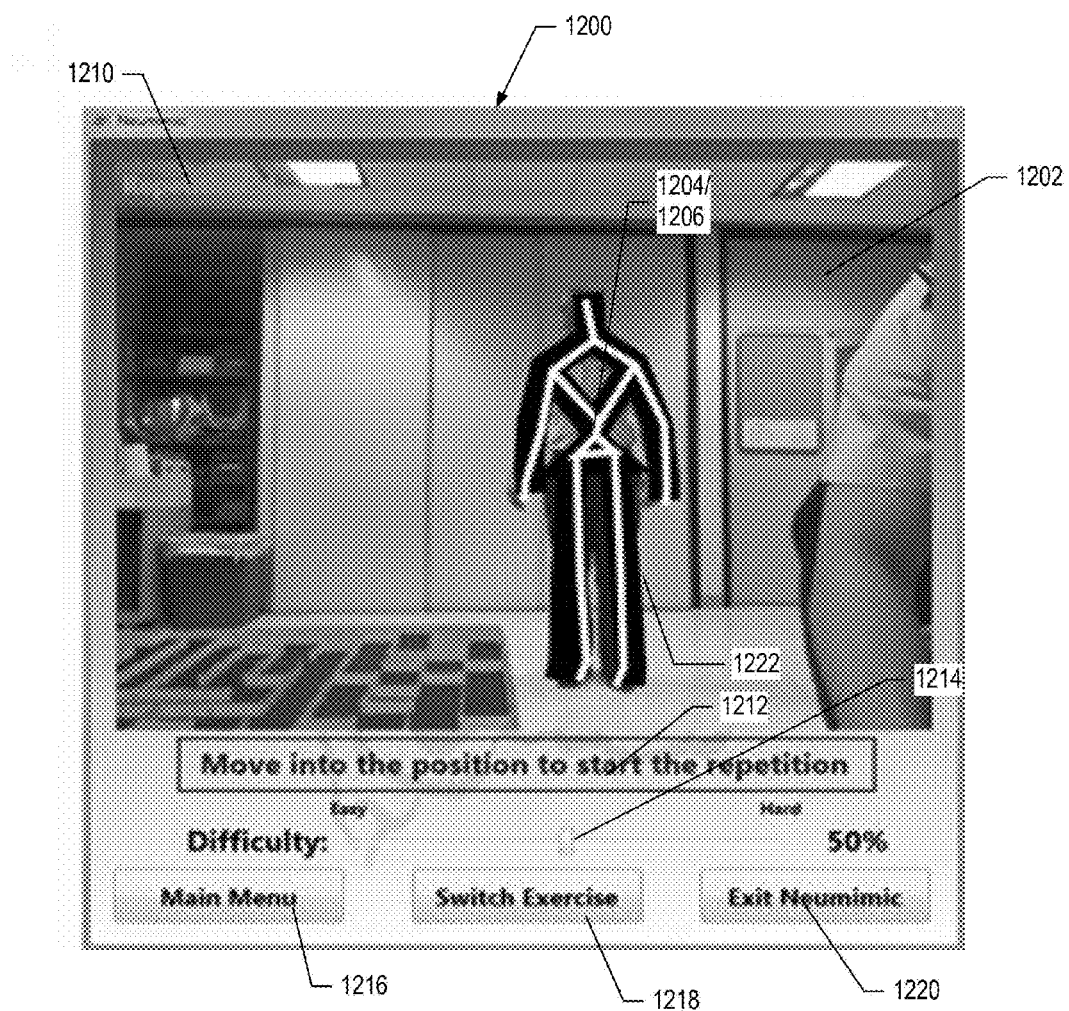
FIG. 12B is a screen shot of an exercise form with alignment between the patient limb trajectory and the target limb trajectory.

The video window 1202 further contains a patient limb trajectory 1206 providing a visual representation of the patient's position and movement of various limb landmarks during the course of performing the exercise. The patient limb trajectory 1206 may be a stick figure as illustrated in FIG. 12 in one aspect. In another aspect, the patient limb trajectory 1206 may be constructed with a different color than the target trajectory 1204 to differentiate the two trajectories. In another aspect, the color of at least a portion of the patient trajectory 1206 may be set to a warning color such as red, as illustrated in FIG. 12, when the patient trajectory 1206 falls outside of a threshold distance from the target trajectory 1204. In this other aspect, any portion of the patient limb trajectory 1206 that falls within a threshold distance of the target trajectory may be represented in a non-alarm color such as green (not shown) or white (as illustrated in FIG. 12B) to signal to the patient that at least a portion of the patient's limbs are following the target trajectory 1204 within the threshold distance.

In addition to color-coding of the patient limb trajectory 1204, the video window 1202 may further include additional warning indicators 1208 to indicate that a particular limb landmark may be outside of a threshold distance relative to the location of the corresponding limb landmark in the target trajectory 1204. By way of non-limiting example, as illustrated in FIG. 12, the exercise module 516 may superimpose a red circle over the image of each limb landmark of the patient joint trajectory 1206 that falls outside of a threshold distance relative to the corresponding limb landmark in the target trajectory 1204. In another aspect, the threshold distance surrounding the target limb trajectory 1204 may be represented by a colored region including, but not limited to a "shadow" region as illustrated in FIG. 12B.

The exercise form 1200 may further include a number of displays and controls. The exercise form 1200 may include a textual message 1212 to provide contextually meaningful instructions to the patient to facilitate the patient's performance of the exercise and/or a repetition counter 1210 to report the repetition of an exercise currently performed by the patient. In another aspect, the exercise form may further include a difficulty slider 1214 that may be translated horizontally to communicate a desired difficulty for the exercise to be performed. In various aspects, a "hard" difficulty may be characterized by more rapid expected movements within a lower threshold distance of the target trajectory 1204. The exercise form 1200 may further include a plurality of controls that may be selected by the patient to navigate among different parts of the physical therapy administration application 130. Selecting the "main menu" control 1216 may transfer the patient back to a main patient menu form 1000, as illustrated in FIG. 10. Selecting the "switch exercise" control 1218 may transfer the patient to the session selection module 510 to select a different exercise via the exercise selection form 1100. Selecting the "exit neumimic" control may cause the patient to exit the physical therapy administration application 130.

The target trajectory 1204, as used herein, refers to a time series of limb landmark positions arranged in frames, each frame including the positions of all target limb landmarks at a single time during the limb movement. In use, the exercise module 516 may display each frame of the target limb trajectory 1204 as illustrated in FIG. 12A. In one aspect, the exercise module displays each frame for a predetermined frame duration. If the patient repositions each limb landmark to match the corresponding target limb landmark positions within the predetermined frame duration, the exercise module 516 advances to the next subsequent frame associated with the next time value of the limb movement. If the patient does not reposition each limb landmark within the predetermined frame duration, the frame freezes for another predetermined frame duration until the patient is able to match all limb landmarks within the desired threshold distance of the corresponding target limb landmarks for that frame.

In various aspects, the frame duration may range from about 2 seconds to about 20 seconds. In another aspect, the frame duration may be about 5 seconds. The frame duration may be specified by the therapist as part of the physical therapy session data, and/or the frame duration may be modified to a faster or slower duration by manipulating the easy/hard slider 1214 of the exercise form 1200.

In various other aspects, the threshold distance from the target limb landmark position within which each corresponding patient limb landmark must fall during an exercise may range from about 10 pixels to about 100 pixels within the video image. In other aspects, the threshold distance may range from about 20 pixels to about 80 pixels. It is to be understood that motion capture devices making use of higher resolution video images may have correspondingly higher numbers of pixels for the corresponding threshold distances in various aspects.

In use, if the frame duration is about 5 seconds and the threshold distance is near 20 pixels, a patient successfully advancing all frames of the exercise will appear to perform a relatively smooth and continuous limb motion.

Patient Motion Capture Module

Referring again to FIG. 5, the physical therapy administration application 130 may include a patient motion capture module 512 in various aspects. The patient motion capture module 512 may act as an interface between the patient motion capture device 128 and the physical therapy administration system 100. For example, as described herein previously, the GUI forms may be used to transmit specific commands to the elements of the patient motion capture device 128. Suitable specific commands to the patient motion capture device 128 include: start motion capture, stop motion capture, clear previous motion capture, save previous motion capture, modulate camera setting such as exposure, focus, zoom, and the like, calibrate the patient motion capture device 128, and; calibrating the camera placement or field of view of the cameras prior to capturing motion.

Patient Performance Module

Referring again to FIG. 5, the physical therapy administration application 130 may include a patient performance module 518 in various aspects. The patient motion capture module 518 may compare the target limb trajectory 1204 and the patient limb trajectory 1206 at a plurality of times throughout the trajectory. During a repetition of an exercise using the exercise module 516, the patient motion capture device 128 may continually capture the positions and motions of the patient's limb landmarks at predetermined time intervals and may compare each measured patient limb landmark location with the most current corresponding target landmark limb position. If the patient succeeds in locating all limb landmarks to within a threshold distance of the target limb landmark position, the exercise module 516 advances the target trajectory to the next frame.

In an aspect, the patient performance module 518 may calculate a patient score for each exercise according to at least one scoring rule. In one aspect, the at least one scoring rule may be a completion rule in which the score for an exercise is equal to the percentage of frames of an exercise advanced by the patient during an exercise according to Eqn. (1):

$$\text{Completion} = \frac{\text{Achieved}_{Frames}}{\text{Total}_{Frames}} * 100\% \qquad \text{Eqn. (1)}$$

In one aspect, the at least one scoring rule may be an accuracy rule in which the score for an exercise is equal to the percentage of frames of an exercise advanced by the patient during an exercise without getting "stuck" due to failing to reposition all patient limb landmarks to within the threshold distance of the corresponding target limb landmarks according to Eqn. (2):

$$\text{Accuracy} = \frac{\text{Total}_{Frames}}{\text{Total}_{Frames} + \text{Stuck}_{Frames}} * 100\% \qquad \text{Eqn. (2)}$$

In other aspects, the patient performance module 518 may calculate a patient score for each exercise according to one or more additional scoring rules. In one aspect, each joint landmark may be weighted relative to other joint landmarks according to a weighted scoring rule in order to emphasize the importance of particular limb landmarks in particular joint movements. Another scoring rule may account for the steadiness and/or rapidity of the limb motion—limb movements that were too rapid or too slow would be scored lower than a limb motion performed at the desired movement speed.

B. Motion Capture Devices

The therapist motion capture device 118 and patient motion capture device 128, in various aspects, may be any known device capable of obtaining a record of a limb movement without limitation. The motion capture device 118/128 may be any known device for non-invasively capturing motion in two dimensions or in three dimensions of the therapist or patient. In one aspect, the motion capture device 118/128 may capture the motion of the therapist or patient without use of markers affixed to the therapist or patient. In various aspects, the motion capture device 118/128 may include one or more cameras, and/or one or more distance sensors or rangefinders to non-invasively obtain measurements used to capture the motion of the therapist or patient. In various additional aspects, the motion capture device 118/128 may be configured to operate effectively in relatively low light conditions. In another aspect, the motion capture device 118/128 may be used to capture the motion of the therapist or patient while wearing a brace. In one aspect, the motion capture device 118/128 may be a KINECT™ system (Microsoft, Inc.).

The record of a limb movement may include any known quantitative description of the positions and movements of various portions of a limb at various times throughout the limb movement. Non-limiting examples of suitable quantitative descriptions of the positions and movements of various portions of a limb include: two-dimensional coordinates of at least two limb landmarks relative to a predefined coordinate system such as horizontal and vertical distances of a landmark relative to a predefined origin; three-dimensional coordinates of at least two limb landmarks relative to a predefined coordinate system such as the horizontal and vertical distances of a landmark relative to a predefined origin as well as distances of the landmark from a reference point; orientation angles between a limb segment and a predetermined axis system; relative angles between adjacent limb segments; and any other known quantitative description of the positions and movements of various portions of a limb.

II. Brace

In various aspects, a brace to facilitate a physical therapy of a patient is disclosed. The brace may include a series of segments joined by adjustable hinges. The adjustable hinges are configured such that the combined range of motion of the series of segments and adjustable hinges falls within a predetermined target limb trajectory associated with a physical therapy as described herein above. In one aspect, the brace may facilitate the patient's positioning of all limb landmarks in an appropriate initial location at the start of a therapy. In various aspects, the adjustable hinges may be configured to independently constrain each hinges range of motion to within a predetermined range, thereby adjusting the overall range of motion and possible limb trajectories of a limb attached to the brace.

In other aspects, the adjustable hinges and/or segments may be instrumented, thereby enabling the ability to independently measure the position of limb landmarks independently of the motion capture device(s) used by the physical therapy administration system 100 as described herein above. In other additional aspects, the adjustable hinges and/or segments may include integrated actuators to assist the limb movement of patients with profound loss of limb motion.

Figure 13:
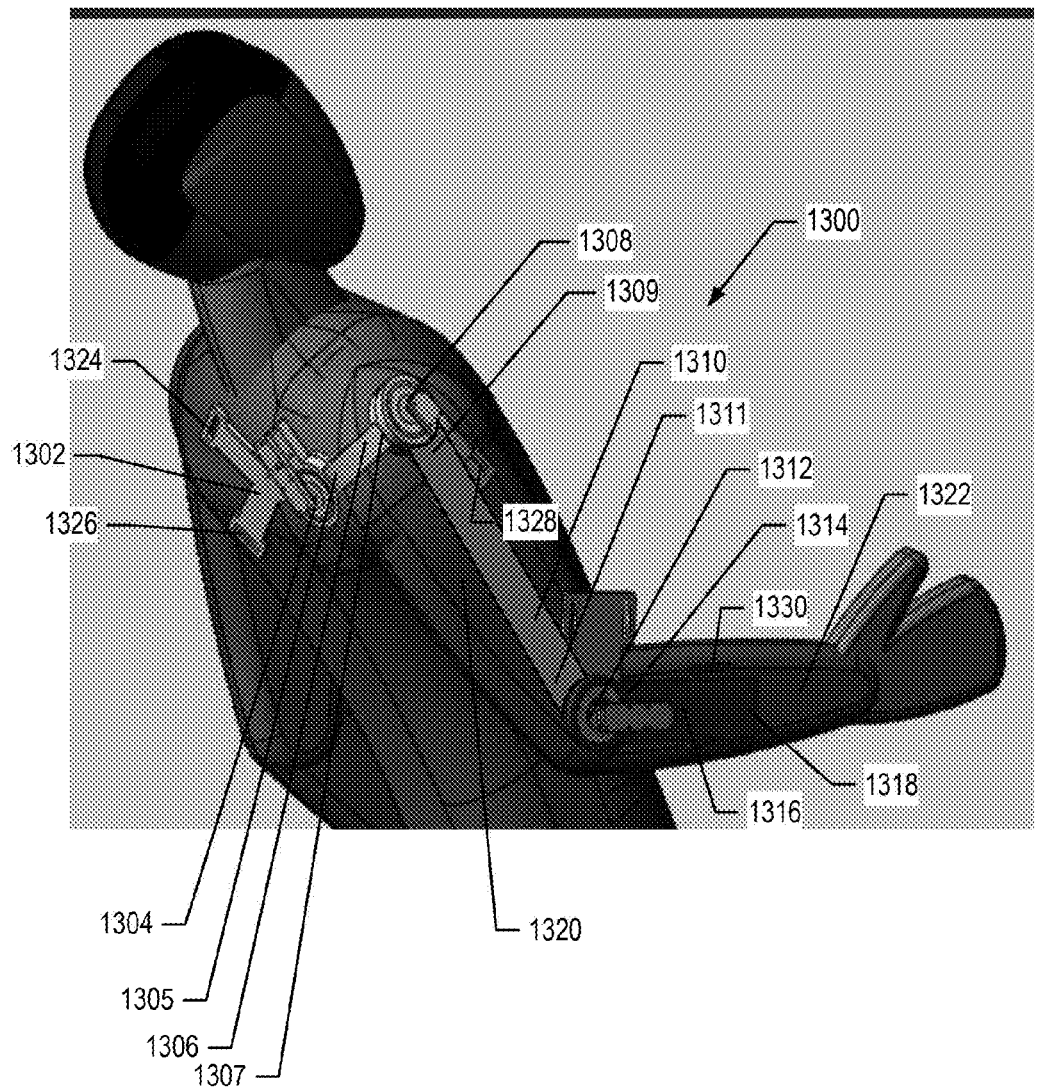
FIG. 13 is a side view drawing of a brace affixed to a patient.

FIG. 13 is a side view of a brace 1300 affixed to a subject in one aspect. In various aspects, the brace 1300 may include a base 1302 with a base hinge 1304 configured to be affixed to a relatively stationary region of a patient including, but not limited to, a torso, a pelvic girdle, or a lower back of a patient. The brace 1300 may further include a base segment 1306 with a proximal base end 1305 operatively coupled to the base hinge 1304 and a distal base end 1307 opposite the proximal base end operatively coupled to a first hinge 1308. In some aspects, the base hinge 1304 and the first hinge 1308 are positioned over the shoulder joint of the patient, thereby constraining the movements of the humerus 1320 to rotations about the base hinge axis (essentially lateral abduction/adduction of the humerus 1320) and rotation about the first hinge axis (essentially dorsal/ventral rotation of the distal end of the humerus 1320).

Referring again to FIG. 13, the brace 1300 may further include a first segment 1310 operatively coupled to the first hinge 1308 at a proximal first end 1309 and operatively coupled to a second hinge 312 at a distal first end 1311 opposite to the proximal first end 1309. The brace 1300 may further include a second segment 1316 operatively coupled at a proximal second end to the second hinge 1312. The distal second end 1318 may be configured to be attached to a portion of the forearm 1322 (i.e. radius and ulnar). In some aspects, the second hinge is position over the elbow joint of the patient, thereby constraining the movements of the forearm to rotations about the second hinge axis (essentially flexion and extension in a plane parallel to a mid-sagittal plane of the patient).

In this aspect, the base hinge 1304, the first hinge 1308 and the second hinge 1312 constrain the overall movement of the arm to within a predefined limb trajectory. In various aspects, the base hinge 1304, the first hinge 1308 and the second hinge 1312 may further include mechanical limits to constrain the overall range of movement of each hinge 1304/1308/1312 to fall within independently predetermined sub-ranges to further constrain the overall limb trajectory.

Figure 14A:
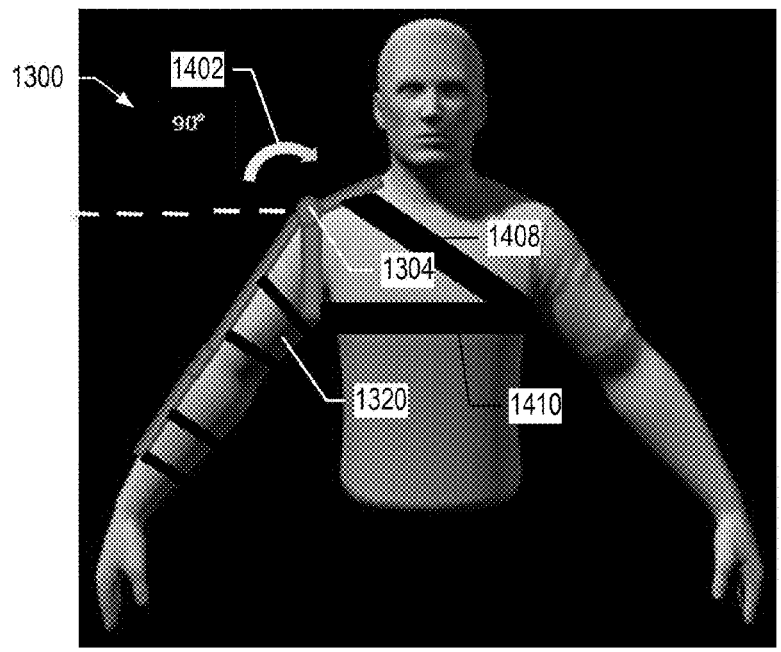
FIG. 14A is a front view of a brace affixed to a patient illustrating the influence of a hinge of the brace on a limb trajectory of the patient in one aspect.
Figure 14B:
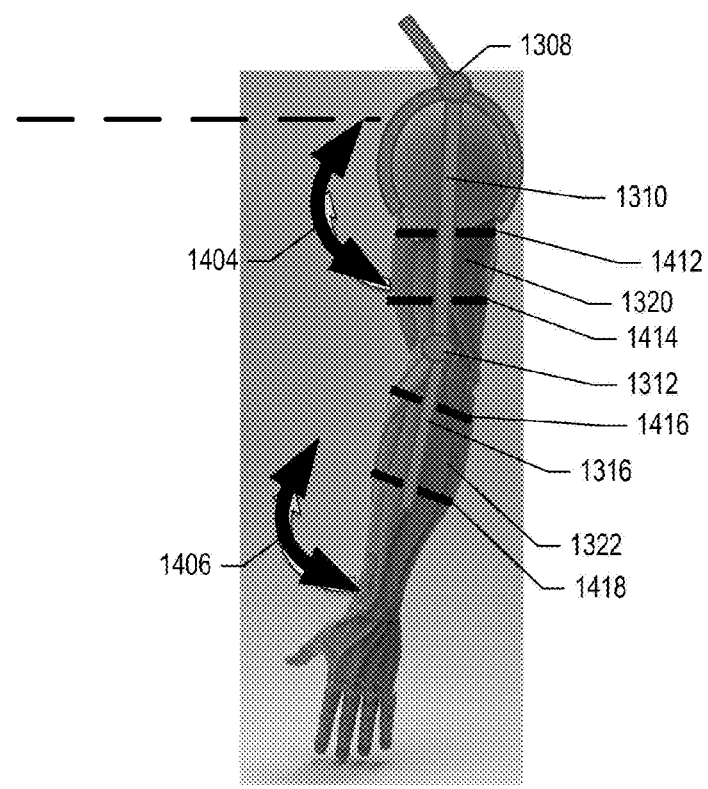
FIG. 14B is a side view of a brace affixed to an arm of a patient illustrating the influence of multiple hinges of a brace on a limb trajectory of the patient in an aspect.

FIGS. 14A and 14B are images depicting a brace 1300A similar to the brace 1300 described previously herein and illustrated in FIG. 13. FIG. 14A is a front view of the patient illustrating that the lateral abduction/adduction 1402 of the humerus 1320 may be constrained to a range from 0 degrees (fully locked hinge) up to about 90 degrees by limiting the range of rotation of the base hinge 1304 in an aspect. Referring to FIG. 14B, the dorsal/ventral movement 1404 of the humerus 1320 may be constrained to a range from 0 degrees up to about 150 degrees by limiting the range of rotation of the first hinge 1308 in another aspect. Referring again to FIG. 14B, the flexion/extension 1406 of the forearm 1322 may be constrained to a range from 0 degrees up to about 150 degrees by limiting the range of rotation of the second hinge 1312 in another aspect.

Figure 15:
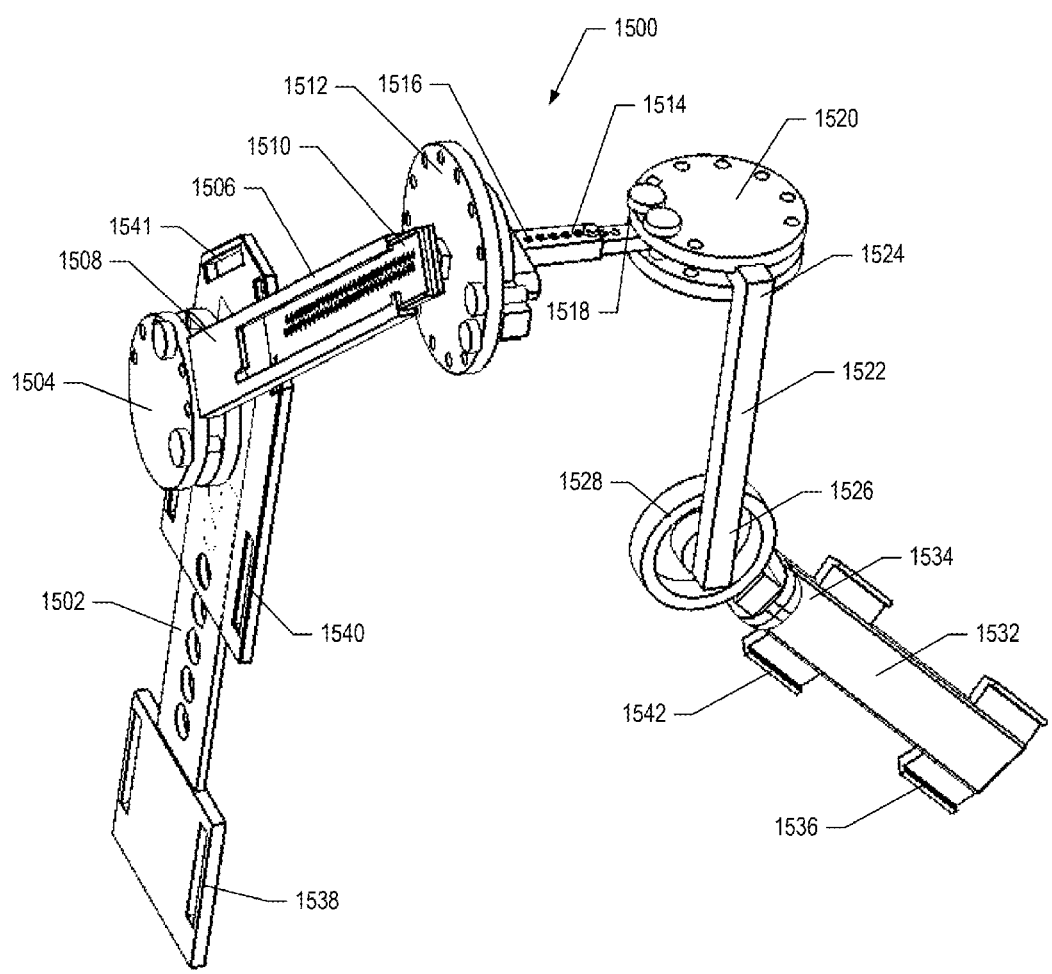
FIG. 15 is a perspective view of a brace in one aspect.

FIG. 15 is a perspective view of a brace 1500 in another aspect with an additional segment and hinge compared to the hinge 1300 described herein previously. Referring to FIG. 15, the brace 1500 may include a two-part adjustable base 1502 configured to attach via straps (not shown) passing through strap fittings 1538, 1540, and 1541 formed in the base 1502, to a stationary portion of the patient including, but to limited to, the torso of the patient. The base 1502 includes a base hinge 1504 at one end that is operatively coupled to a proximal base end 1508 of a base segment 1506. The opposite distal base end 1510 is operatively coupled to a first hinge 1512. The second segment 1514 is operatively coupled to the first hinge 1512 and a second hinge 1520 at a second proximal end 1516 and an opposed second distal end 1518, respectively. The opposite third proximal end 1524 and third distal end 1528 are operatively coupled to the second hinge 1520 and a third hinge 1528. The third hinge 1528 is operatively coupled to a third proximal end 1534 of a third segment 1532. The third element 1532 is further configured to attached to a forearm (not shown) of a patient via straps (not shown) threaded through strap fittings 1536 and 1542.

I. Adjustable Base and Segments

Figure 16:
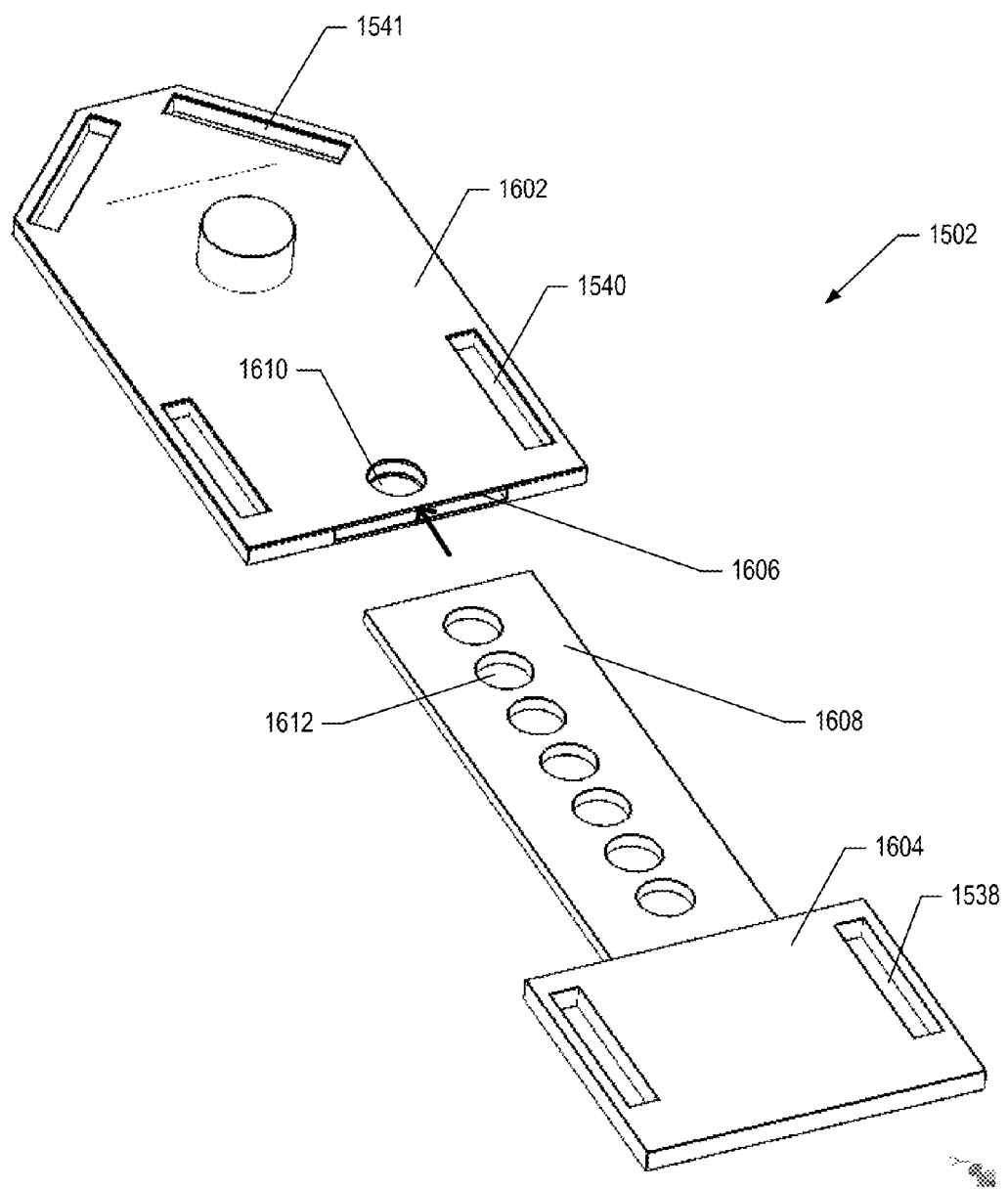
FIG. 16 is an exploded view of a base of a brace in an aspect.

Referring again to FIG. 15, the base 1502, base segment 1506 and first segment 1514 of the brace 1500 may include features that may enable these segments to adjust in length to compensate for individual differences in bone lengths, thereby enhancing the precise placement of the hinges 1504/1512/1520/1530 to constrain the limb trajectory in a predetermined manner as described previously herein. In various aspects, the base 1502 and segments 1506/1514 may include features to increase or decrease each segment's length in a locking manner. FIG. 16 is an exploded view of the base 1502 of the brace 1500 described herein previously in FIG. 15. Referring to FIG. 16, the base 1502 includes an upper portion 1602 and a lower portion 1604. The upper portion includes a channel 1606 formed within the upper portion and opening at one end of the upper portion 1602. A tongue 1608 slides within the channel 1606 and mating bores 1610 and 1612 formed in the upper portion 1602 and tongue 1608 may overlap and be fixed in place by inserting a peg, pin, or any other suitable fastener through the overlapped bores 1610-1612. The multiple bores 1612 formed in the tongue 1608 permit the tongue to be inserted to varying degrees into the channel 1606 and held in place as described herein previously.

Figure 17:
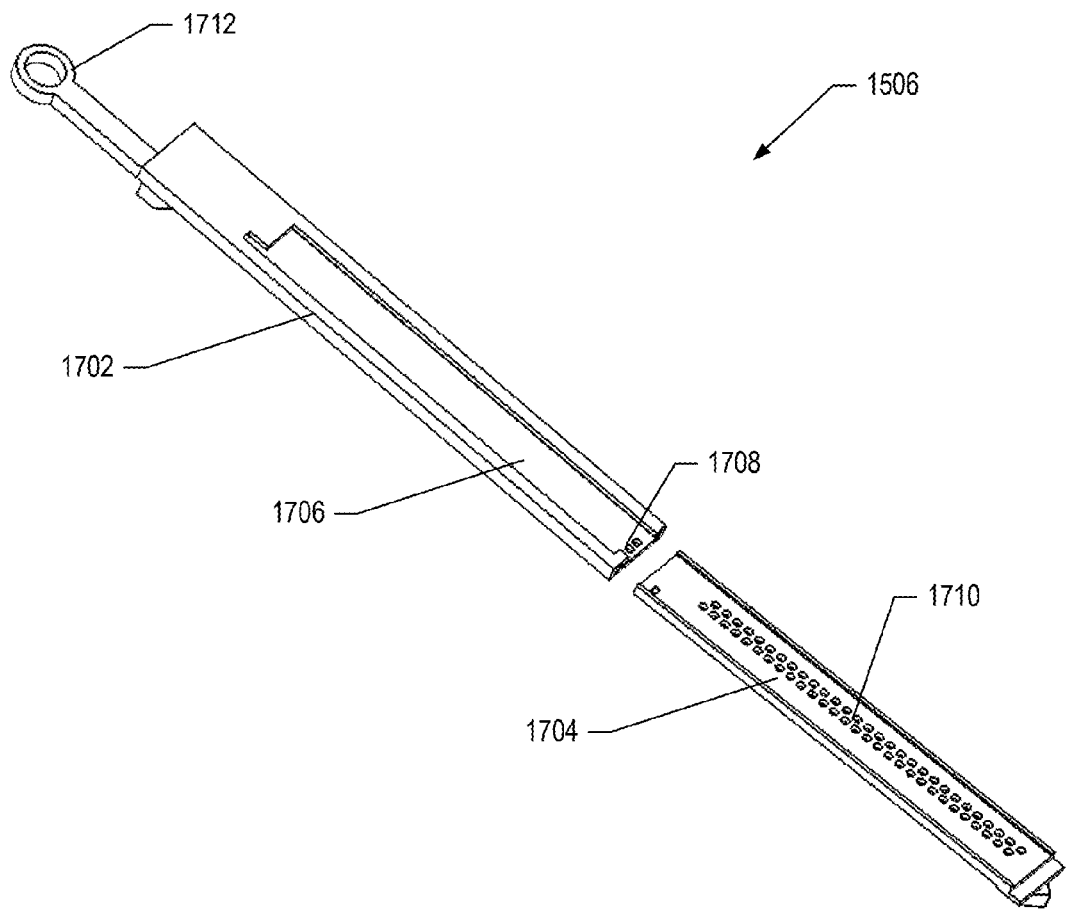
FIG. 17 is an exploded view of a base segment of a brace in an aspect.

FIG. 17 is an exploded view of the base segment 1506 showing a proximal portion 1702 ending in a base hinge fitting 1712 and a distal portion 1704. The proximal portion 1702 includes a channel 1706 within which the distal portion 1704 may slide. The proximal portion 1702 has a single row of relatively small bores 1708 formed near an open end of the channel 1706. The distal portion 1704 has a plurality of rows of bores 1710 matched in size and spacing to the bores 1708 of the proximal portion 1702. The distal portion 1704 may be inserted into the channel 1706 of the proximal portion 1702 to a desired degree and a peg, pin, or any other suitable fastener may be inserted through the overlapping bores 1708/1710 to fix the length of the base arm 1506.

Figure 18:
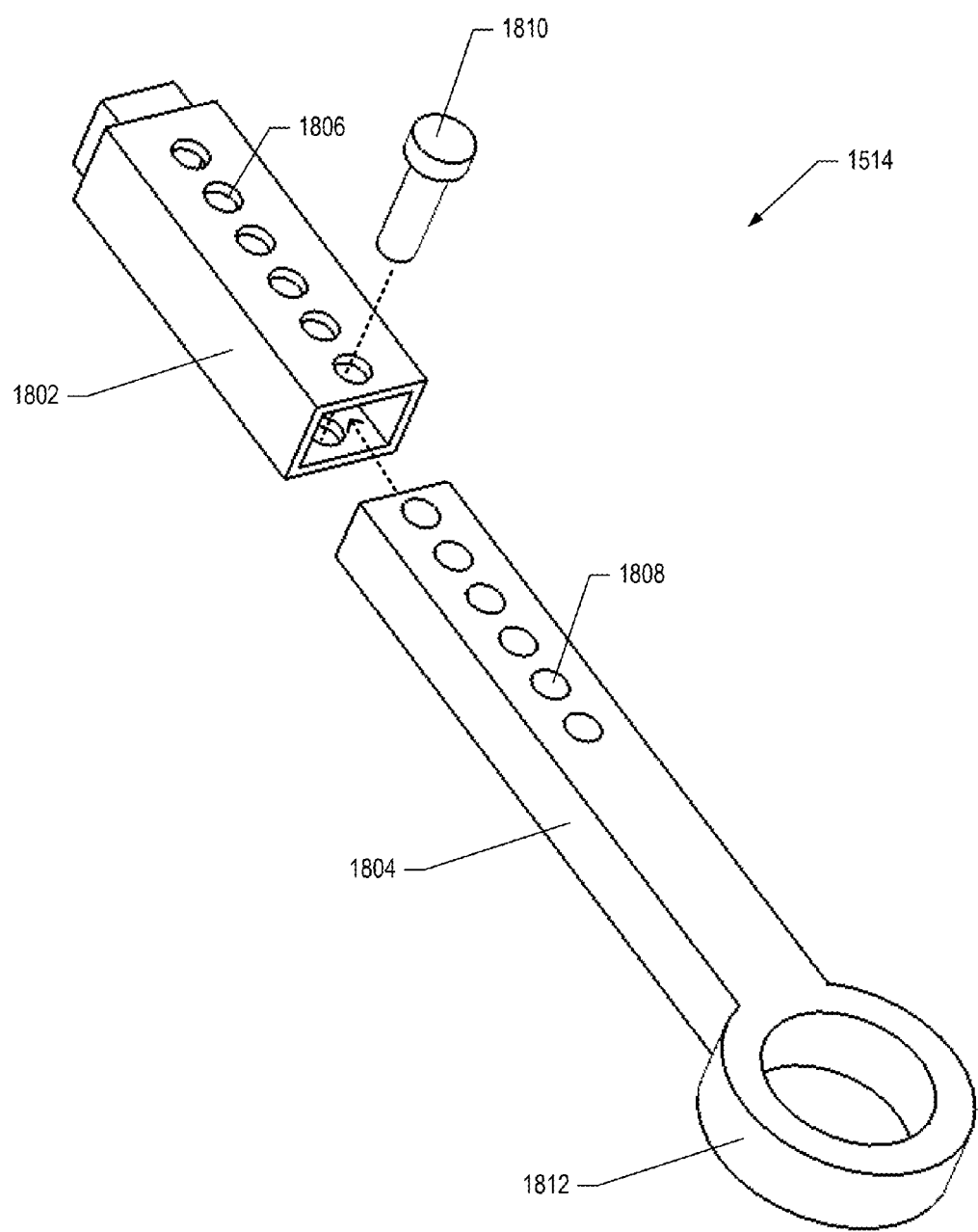
FIG. 18 is an exploded view of a first element of a brace in an aspect.

FIG. 18 is an exploded view of the first segment 1514 described previously in FIG. 15. Referring to FIG. 18, the first segment 1514 includes a proximal sleeve 1802 with a plurality of proximal bores 1806 passing through the full depth of the proximal sleeve 1802. The first segment further includes a distal portion 1804 ending at a second hinge fitting 1812. The distal portion 1804 includes a plurality of distal bores 1808 matched in spacing and dimension to the plurality of proximal bores 1806. In an aspect, the distal portion 1804 may be inserted into the proximal sleeve 1802 to a desired degree, and the resulting segment length may be locked into place by inserting any suitable fastener including, but not limited to, a peg 1810 through a pair of overlapping proximal and distal bores 1806/1808.

II. Hinge Rotation Stops

In various aspects described herein above, the hinges 1504/1512/1520/1528 may include adjustable mechanical stops to constrain the range of rotation of each hinge to a predetermined subrange. In one aspect, the adjustable mechanical stops may be used lock the hinge into an immobilized state, thereby maintaining a fixed angle between the two segments to which the hinge is attached. By way of non-limiting example, referring to FIG. 15, the base hinge 1504 may be locked in an immobilized position to maintain the first hinge 1512 and second hinge 1520 in relatively fixed positions relative to the shoulder of the patient. In addition, the locked base hinge 1504 may prevent the patient from other undesired movements including, but not limited to, shoulder shrugging while performing an exercise as part of a physical therapy session.

Any known method of providing mechanical stops for a rotating hinge coupling may be used as adjustable mechanical stops without limitation. In one aspect, the adjustable mechanical stops may be a pair of mechanical fasteners including, but not limited to, pins, pegs, bolts, and the like inserted through a pair of bores, holes, and/or channels formed in a structural element of a hinge. In an aspect, a plurality of bores, holes, and/or channels may be provided to enable a range of adjustments to the range of motion of each hinge.

Figure 19:
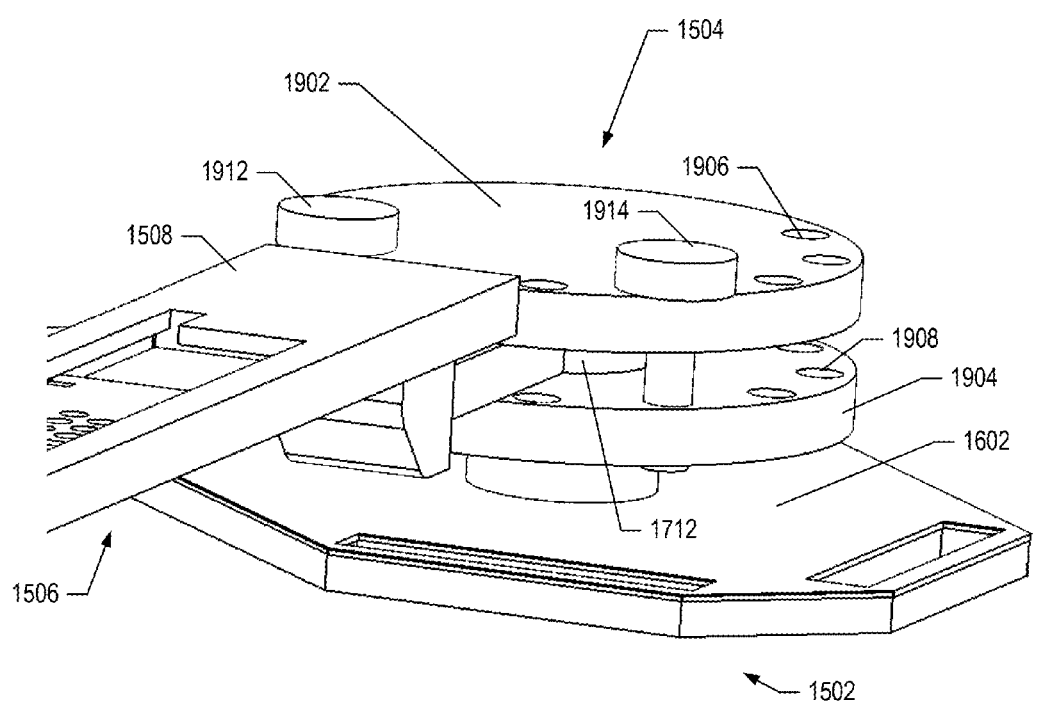
FIG. 19 is a side view of a base hinge of a brace in an aspect.

By way of non-limiting example, the base hinge 1504 may include an adjustable mechanical stop in the form of pegs inserted through bores formed within the base hinge 1504. FIG. 19 is a close-up side view of a base hinge 1504 and operatively coupled base segment 1506. The base hinge 1504 may include a top plate 1902 and a bottom plate 1904 with the base hinge attachment fitting 1712 situated between the two plates 1902/1904. The top plate 1902 may include a plurality of top bores 1906 spaced circumferentially around at least a portion of the top plate 1902. The bottom plate 1904 may include a plurality of bottom bores 1908 similarly spaced and vertically aligned with the plurality of top bores 1906. A first pin 1912 and a second pin 1914 may be inserted through a vertically aligned top bore 196 and bottom bore 1908, thereby forming a pair of mechanical stops to limit the movement of the base segment 1506 relative to the base hinge 1504 and attached base 1502.

Figure 20:
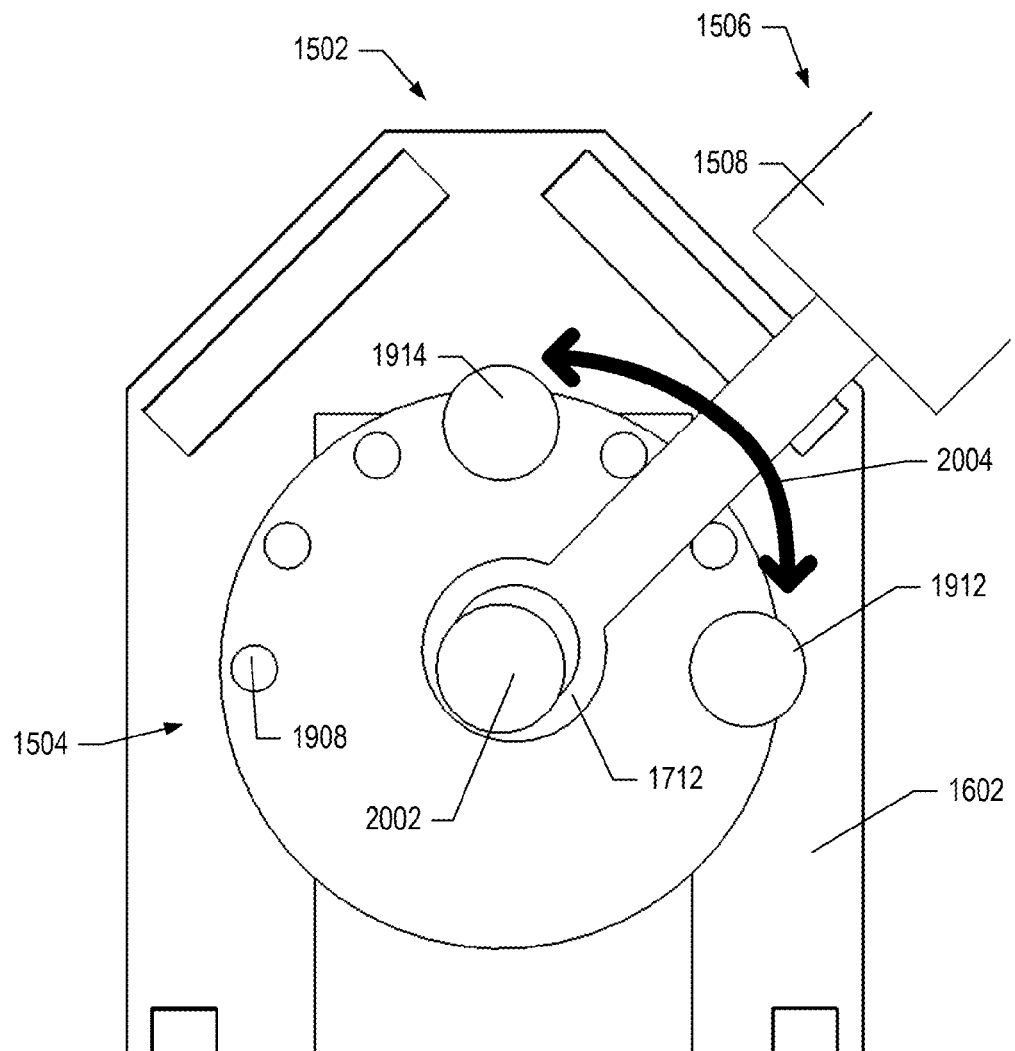
FIG. 20 is a top view of a base hinge mounted on an upper portion of a base of a brace, in which the upper plate of the hinge is removed.

FIG. 20 is a top view of the base hinge 1504 with the top plate 1902 removed. The base hinge attachment fitting 1712 may fit over a hub 2002 of the base hinge 1504, forming a coupling that may freely rotate in a plane defined by the top plate 1902 and bottom plate 1904 of the base hinge 1504. The first pin 1912 and second pin 1914 form mechanical stops to limit the range of rotation 2004 of the base segment 1506 relative to the base hinge 1504. In an aspect, the first and second pins 1912/1914 may be inserted through adjacent bores 1906/1908 to lock the base segment 1506 in a fixed position within the base hinge 1504.

Figure 21:
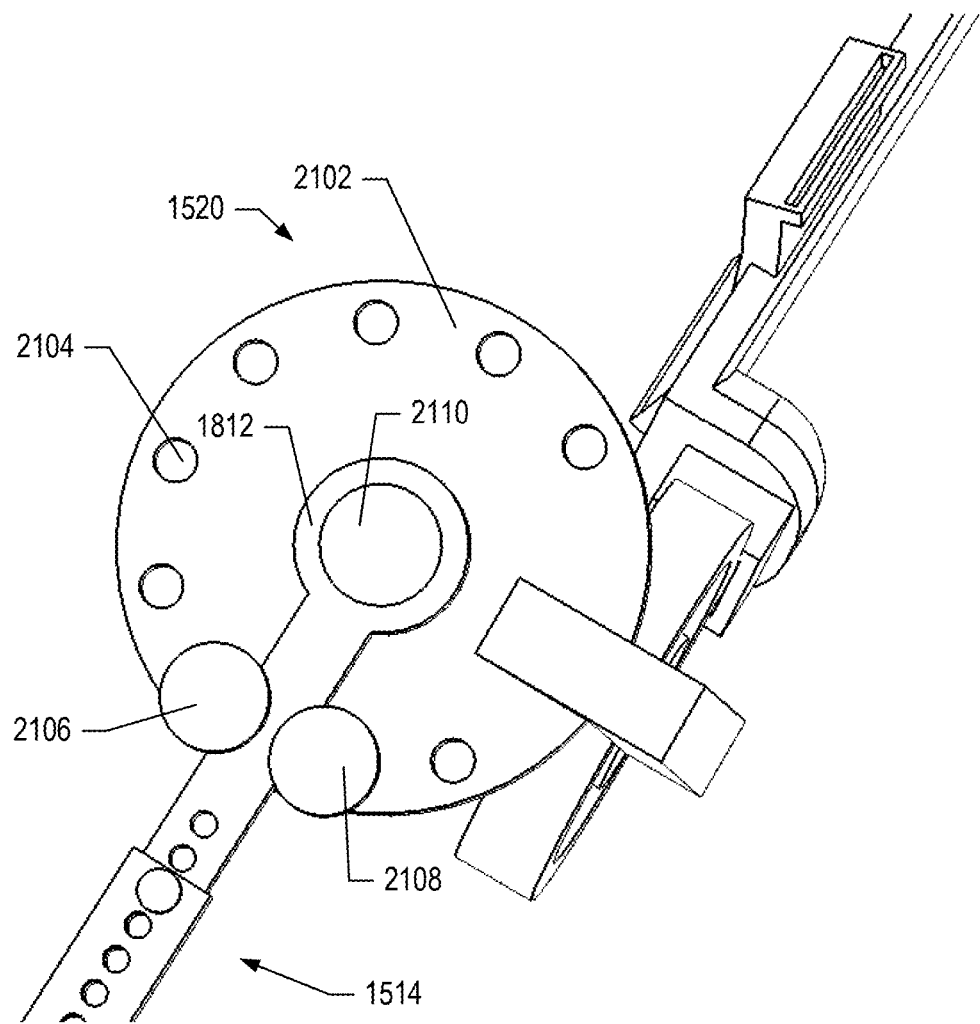
FIG. 21 is a top view of a second hinge in which the upper plate of the hinge is removed.

By way of another non-limiting example, FIG. 21 is a top view of the second hinge 1520 with the top plate (not shown) removed. The second hinge attachment fitting 1812 may fit over a hub 2110 of the second hinge 1520, forming a coupling that may freely rotate in a plane defined by the top plate and bottom plate 2102 of the second hinge 1520. The bottom plate 2102 may include a plurality of bottom bores 2104 distributed circumferentially around at least a portion of the bottom plate 2102. As illustrated in FIG. 21, a first pin 2106 and second pin 2108 are inserted into adjacent bottom bores 2104 to form mechanical stops immediately adjacent to the to limit the range of rotation 2004 of the base segment 1506 relative to the base hinge 1504. In an aspect, the first and second pins 1912/1914 may be inserted through adjacent bores 1906/1908 to lock the first segment 1514 in a fixed position within the second hinge 1520.

In other aspects, the bores within the hinges may be provided with markings to indicate the position of each bore within a plurality of bores corresponding to each hinge. In an aspect, the therapist may specify the range of motion of the brace 1500 by specifying the positions of each mechanical stop in each hinge of the brace 1500 using the bore markings.

III. Attachment of Brace to Patient

In other aspects, one or more segments of the brace may be configured to attach to a portion of the patient. In one aspect, the most proximal portion of the brace may be attached to a stationary location to provide a mechanically fixed point relative to which the remaining segments of the brace may move. Referring to FIG. 13, the base 1302 of the brace 1300 may be attached to the torso of the patient. Referring to FIGS. 13 and 14A, the base 1302 may be attached to the torso of the patient by one or more straps 1408 and 1410 wrapped around the torso. The ends of the straps 1408/1410 may be threaded through corresponding strap attachment fittings 1324 and 1326 on the base 1302. In another aspect, a base of a brace may be configured for attachment to a stationary object including, but not limited to: a wheelchair, a wall, a bed, a table, and any other suitable stationary object without limitation. In this aspect, the attachment to a stationary object enables the use of the brace by patients with relatively limited mobility, such as wheelchair-bound or bed-bound patients.

In other aspects, one or more of the more distal segments of the brace may be configured for attachment to one or more portions of the limb of a patient. Referring to FIG. 14B, first segment 1310 and second segment 1316 may be configured for attachment to the upper arm 1320 and forearm 1322, respectively, of the patient using straps 1412/1414/1416/1418. The ends of straps 1412/1414 may be threaded through strap attachment fittings 1328 provided on the first segment 1310, and the ends of straps 1416/1418 may be threaded through strap attachment fittings 1330 provided on the second segment 1316.

Any known devices and methods for attaching external equipment to the bodies and/or limbs of patients may be used to attached at least a portion of the brace to the patient including, but not limited to: straps such as Velcro straps, adhesive tape, reversibly adhesive surfaces of one or more segments of the brace, and any other known suitable attachment device or method.

IV. Sensors and Actuators

In other aspects, any one or more of the hinges and/or segments of the brace 1500 may further include sensors to monitor the position and movements of at least a portion of the brace 1500. In an aspect, the sensors may measure the position and movements of limb landmarks corresponding to the limb landmarks measured by the motion capture devices as described previously herein above. In one aspect, the sensors may measure a plurality of limb landmarks that may be used to calibrate the corresponding measurements of limb landmarks obtained using a motion capture device. In another aspect, the sensors may measure a plurality of limb landmarks that may be used in place of the measurements obtained by a motion capture device in the physical therapy administration system 100 described herein above.

Any known device and/or method of measuring a position, rotation, and/or acceleration may be used as a sensor within the brace without limitation. In one aspect, a rotational sensor including, but not limited to, a rotary encoder may be included within one or more hinges of the brace to monitor the angles of each segment relative to each hinge. In another aspect, any one or more of the hinges and/or segments of the brace may include an attached accelerometer to monitor the positions of the one or more of the hinges and/or segments.

In other additional aspects, the one or more hinges may further include actuators to provide assistance to the patient to perform a limb movement associated with an exercise as part of a physical therapy session. Any known actuator capable of generating torque within a hinge may be included in the one or more hinges of the brace without limitation. In one aspect, one or more actuators may be activated at selected times to provide assistance to the patient during an exercise. In one aspect, the actuators may be activated using feedback from the physical therapy administration system 100. By way of non-limiting example, if a patient is unable to reposition all limb landmarks to match the target limb trajectory as measured by the physical therapy administration system 100, the physical therapy administration system 100 may activate one or more actuators in order to correctly reposition all limb landmarks. In another aspect, the actuators may be activated in a sequence such that the brace may move through a limb trajectory associated with an exercise to demonstrate the movement to the patient.

III. Methods of Administering Physical Therapy

Figure 22:
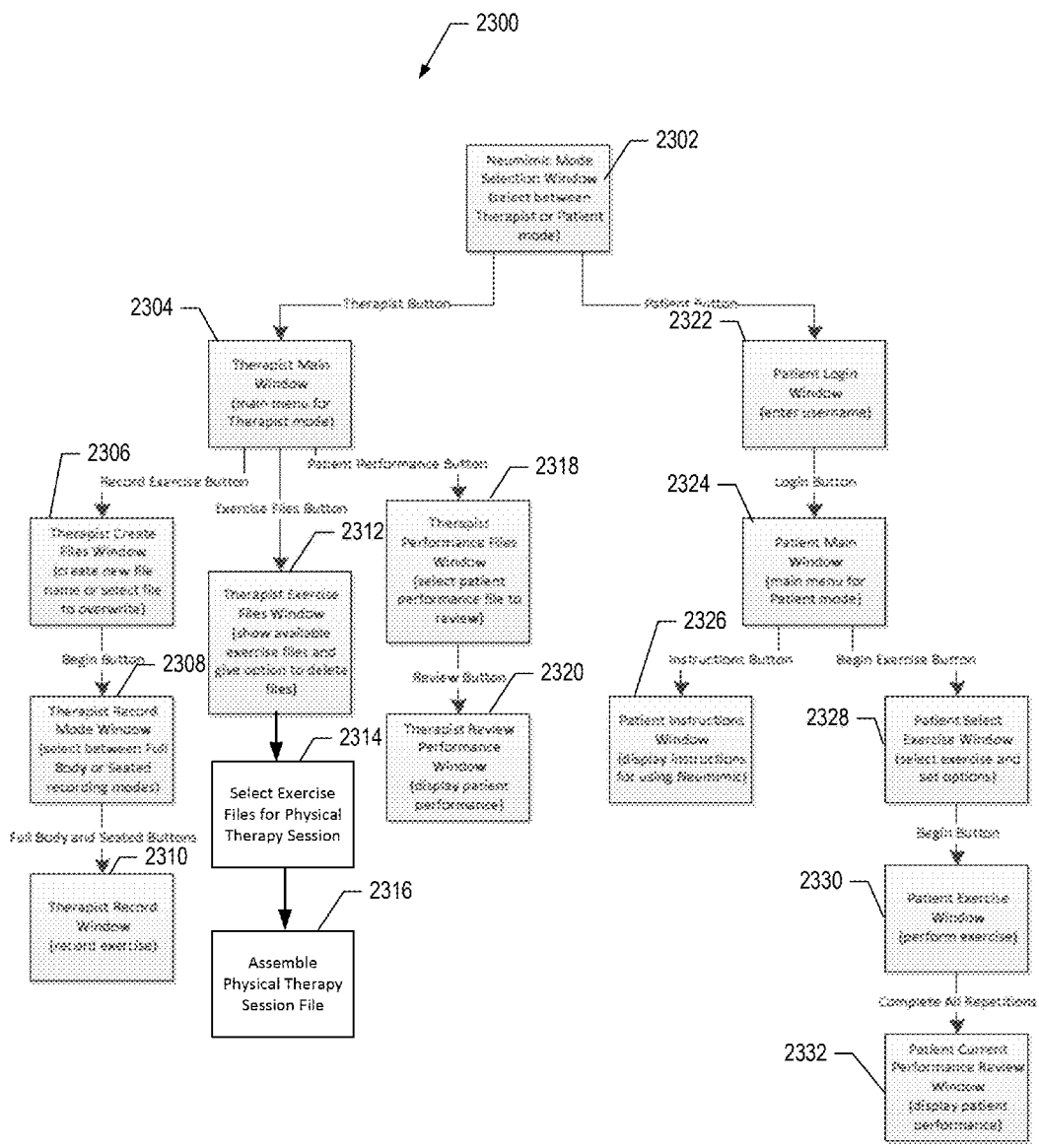
FIG. 22 is a flow chart illustrating a method of administering a physical therapy to a patient using a physical therapy administration system.

In various aspects, the physical therapy administration system 100 may be used to remotely administer a physical therapy to a patient. FIG. 22 is a flow chart illustrating a method 2300 of administering a physical therapy to a patient in need in one aspect. In one aspect, the therapist may access a menu of therapist options at step 2302 by clicking a control button such as the "therapist" control 1006 the main menu form 1000 illustrated in FIG. 10. In an aspect, access to the therapist options may be protected by password access or any other security method to limit access to the therapist options to the therapist and other users authorized by the therapist only.

Referring again to FIG. 22, the therapist may access the exercise administration module 502 (see FIG. 5) from the menu of therapist options at step 2304. The therapist may create a new exercise file to store a new exercise to be recorded by the therapist at step 2306. For example, the therapist may create a new file by clicking a "new recording" control 706 of an exercise recording form 700 as illustrated in FIG. 7. In another aspect, the therapist may choose to overwrite an existing file if, for example, the existing file was determined to be unsuitable by the therapist.

Referring again to FIG. 22, the therapist may initiate the recording of an exercise at step 2308. The therapist motion capture module 504 (see FIG. 5) may provide a functional interface for operating the equipment of the motion capture device via the exercise recording form 700. Referring to FIG. 7, the exercise recording form 700 may include a video window 704 displaying the view of the camera of the motion capture device. The therapist may prepare for recording an exercise using the view displayed in the video window 704 as a guide. For example, the therapist may move to a position visible by the camera of the motion capture device, adjust lighting, eliminate distracting background objects, focus the camera, and make any other necessary preparations prior to recording the exercise.

Referring again to FIG. 22, the therapist may record the exercise at step 2310. The camera of the motion capture device may be activated by any known device or method including, but not limited to: a remote control device, a GUI control, manually activating the camera, and voice activation. In one aspect, the camera may be voice activated by the therapist motion capture module 504 (see FIG. 5) as described previously herein in connection with FIG. 7. The exercise file containing the exercise file may be stored in the database component 150 (see FIG. 1) for subsequent review and/or use.

The exercise file may contain the positions and movements of various limb and body landmarks of the therapist captured by the motion capture device during the recording of the exercise. In one aspect, the exercise file may contain a plurality of frames, each frame corresponding to one discrete time during the exercise. Each frame may include data representing the positions of the plurality of limb and body landmarks at the one discrete time. The exercise file may be reviewed by the therapist and/or included in a physical therapy session assembled by the therapist and transferred to the patient.

Referring again to FIG. 22, the therapist may access previously recorded exercises stored in the database component 150 at step 2312. The therapist may review, edit, recopy, rename, or delete any exercise file at step 2312. For example, the therapist may review an exercise file, crop out any unnecessary portions, adjust video parameters such as contrast and/or brightness, and store the updated exercise file for subsequent use.

Referring again to FIG. 22, the therapist may select one or more exercise files from the database component 150 at step 2314. The one or more exercise files, along with any additional information provided by the therapist, may be assembled by the therapist at step 2316 and stored as a physical therapy session file in the database component 150 using the session administration module 506 (see FIG. 5). Non-limiting examples of additional information to be included in a physical therapy session file include: objectives of each exercise, number of repetitions of each exercise, and/or settings for one or more adjustable hinges of a brace as described herein above. The physical therapy session files may be accessed by the patient using the physical therapy administration system 100.

The therapist may access the patient monitoring module 508 to review performance files generated by the patient performance module 518 (see FIG. 5) at step 2318. For example, the therapist may interact with a performance review form 900A illustrated in FIG. 9B. The therapist may select a particular exercise for a patient from the exercise selection window 920. The therapist may then review the performance of the patient at step 2320 of FIG. 22.

Referring again to FIG. 22, the patient may initiate use of the physical therapy administration system 100 at step 2302. The patient may access the patient options at step 2322 by logging in and entering a password at step 2322. The patient may interact with a menu of patient options at step 2324, or view instructions at step 2326. For example, the patient may interact with a main patient menu form 1000 as illustrated in FIG. 10.

The patient may access the session selection module 510 to select an exercise at step 2328. For example, the patient may click a "select exercise" control 1002 of a main patient menu form 1000 as illustrated in FIG. 10. The physical therapy administration system 100 may identify all physical therapy session files and associated exercise files assigned to the patient and transfer information for constructing an exercise selection menu to the patient's computing device. The patient may select an exercise by interacting with the exercise selection form 1100 as illustrated in FIG. 11. By way of non-limiting example, the exercise selection form may include an exercise menu window containing a list of entries identifying all available exercises for use by the patient. In an aspect, the exercise selection form 1100 may further include a visual representation of each exercise including, but not limited to an avatar as illustrated in FIG. 11, a diagram, an animation, and any other suitable visual representation of an exercise.

Referring again to FIG. 22, the patient may access the exercise module 516 to perform the selected exercise at step 2330. For example, the patient may click an entry 1104 of the exercise selection window 1104 as illustrated in FIG. 11 to select an exercise and enter an exercise form 1200, illustrated in FIG. 12. The exercise form 1200 may interact with the patient motion capture module 512 to operate a motion capture device used to monitor the patient's movements during the exercise. The patient may interact with the exercise form 1200 as described previously herein to operate the motion capture device and to perform the exercise. For example, the patient may reposition into an appropriate starting position and move a limb through a limb trajectory according to visual cues provided by a target trajectory 1204 superimposed over a video image obtained by the motion capture device, as displayed in a video window 1202 of the exercise form 1200. In an aspect, the target trajectory 1204 may be generated for display in the video window 1202 using the data describing limb landmark positions in the exercise file previously recorded by the therapist at step 2308.

Referring again to FIG. 22, the patient may access the session review module 514 to review performance information for completed exercises at step 2332. In one aspect, the patient may interact with a performance review form 900 as illustrated in FIG. 9A. The performance review form 900 may display information characterizing each previously completed exercise including, but not limited to: the name of the exercise, the number of repetitions, the degree of difficulty of the exercise, and scores for each exercise as generated by the patient performance module 518 including a completion score described previously herein.

Having described several embodiments, it will be recognized by those skilled in the art that various modifications, alternative constructions, and equivalents may be used without departing from the spirit of the disclosure. Those skilled in the art will appreciate that the presently disclosed embodiments teach by way of example and not by limitation. Therefore, the matter contained in the above description or shown in the accompanying drawings should be interpreted as illustrative and not in a limiting sense. Additionally, a number of well-known processes and elements have not been described in order to avoid unnecessarily obscuring the disclosure. The following claims are intended to cover all generic and specific features described herein, as well as all statements of the scope of the present method and system, which, as a matter of language, might be said to fall therebetween.

What is claimed is:

1. A physical therapy administration system for a remote administration of at least one physical therapy session to a patient, the system comprising:
    a computing device comprising at least one processor;
    at least one dataset;
    a CRM configured with a physical therapy administration application comprising a plurality of modules executable by the at least one processor, the plurality of modules comprising:
        a exercise administration module to record at least one exercise comprising a target limb trajectory using a motion capture device;
        an exercise module configured to:
            retrieve an exercise of the at least one exercises;
            generate a visual display representing the exercise;
            record a patient response comprising a patient limb trajectory performed to follow the visual display using the motion capture device;
            calculate a difference between the patient response and the exercise; and
            signal the patient if the difference exceeds a threshold difference; and
        a session review module configured to produce:
            a graph determining a target trajectory of a limb landmark and the corresponding patient trajectory of the same limb landmark,
            a graph of the differential displacement of the patient trajectory and target trajectory of the same limb landmark,
            a graph of a target trajectory and a patient trajectory of a common limb angle, and
            a graph of the difference in limb angles of the patient relative to the limb angles during the target limb trajectory;
    the motion capture device.

2. The system of claim 1, wherein the physical therapy administration application further comprises a GUI module to generate one or more forms used to receive inputs to the system and to deliver output from the system.

3. The system of claim 1, wherein the motion capture device is configured to record the exercise, and the system further comprises a second motion capture device used by the patient to record the patient response.

4. The system of claim 1, wherein:
    each exercise of the at least one exercises comprises a plurality of frames;
    each frame corresponds to a single time during the duration of a limb movement;
    each frame comprises a plurality of spatial locations recorded by the motion capture device; and
    each spatial location corresponds to each limb landmark of a plurality of limb landmarks.

5. The system of claim 1, wherein:
    the patient response comprises a plurality of patient frames;
    each patient frame corresponds to one frame of the exercise;
    each patient frame comprises a plurality of patient spatial locations recorded by the motion capture device; and
    each patient spatial location corresponds to each spatial location of a limb landmark of the exercise.

6. The system of claim 1, wherein:
    the difference between the patient response and the exercise comprises a plurality of difference frames;
    each difference frame corresponds to a frame of the exercise;
    each difference frame comprises a plurality of position errors; and
    each position error comprises a difference between the spatial location and the corresponding final patient spatial location for each limb landmark in the frame of the exercise.

7. The system of claim 1, wherein the exercise module signals the patient if any one of the position errors exceeds the error threshold.

8. The system of claim 1, wherein the at least one scoring rule comprises at least one of:
    a position error rule comprising summing all position errors for all difference frames of the patient response;
    a completion rule comprising calculating a completion percentage according to:

$$\text{Completion Percentage} = \frac{\text{Achieved}_{Frames}}{\text{Total}_{Frames}} * 100\%,$$

wherein Achieved$_{frames}$ comprises all exercise frames advanced prior to the frame duration and Total$_{frames}$ comprises the total number of exercise frames in the exercise; and
    an accuracy rule comprising calculating an accuracy according to:

$$\text{Accuracy} = \frac{\text{Total}_{Frames}}{\text{Total}_{Frames} + \text{Stuck}_{Frames}} * 100\%,$$

wherein Stuck$_{frames}$ comprises the number of exercise frames advanced after a display time exceeding the frame duration.

9. A method of administering a physical therapy of a subject, the method comprising:
    recording at least one exercise comprising a target limb trajectory using a motion capture device;
    generating a visual display representing the exercise;
    recording a patient response comprising a patient limb trajectory performed to follow the visual display using the motion capture device;
    calculating a difference between the patient response and the exercise;
    signaling the patient if the difference exceeds a threshold difference;
    calculating at least one performance score for the patient response according to at least one scoring rule; and
    producing:
        a graph determining a target trajectory of a limb landmark and the corresponding patient trajectory of the same limb landmark,
        a graph of the differential displacement of the patient trajectory and target trajectory of the same limb landmark,
        a graph of a target trajectory and a patient trajectory of a common limb angle, and
        a graph of the difference in limb angles of the patient relative to the limb angles during the target limb trajectory.

10. The method of claim 9, wherein:
each exercise of the at least one exercises comprises a plurality of frames;
each frame corresponds to a single time during the duration of a limb movement;
each frame comprises a plurality of spatial locations recorded by the motion capture device; and
each spatial location corresponds to each limb landmark of a plurality of limb landmarks.

11. The method of claim 9, wherein the plurality of limb landmarks are chosen from any one or more of: a shoulder, an elbow, a wrist, an ankle, a knee, a hip, a hand, a foot, a finger, or a toe.

12. The method of claim 9, wherein the visual display generated by the patient exercise module comprises:
a plurality of target images, each target image comprising the plurality of spatial locations from one frame of the plurality of frames, wherein each target image is displayed for up to a frame duration in a time sequence comprising all target images corresponding to all frames of the plurality of frames; and
a patient image comprising a plurality of patient spatial locations measured by the motion capture device in real time and superimposed over each target image in the time sequence.

13. The method of claim 9, wherein the target image is chosen from one of: a plurality of discrete points, each point corresponding to a spatial location of a limb landmark; a stick figure comprising the plurality of discrete points connected by one or more lines, each line representing a torso or appendage; or an avatar with limbs positioned according to the plurality of spatial locations.

14. The method of claim 9, wherein:
the difference between the patient response and the exercise comprises a plurality of difference frames;
each difference frame corresponds to a frame of the exercise;
each difference frame comprises a plurality of position errors; and
each position error comprises a difference between the spatial location and the corresponding final patient spatial location for each limb landmark in the frame of the exercise.

15. The method of claim 9, wherein the at least one scoring rule comprises at least one of:
a position error rule comprising summing all position errors for all difference frames of the patient response;
a completion rule comprising calculating a completion percentage according to:

$$\text{Completion Percentage} = \frac{\text{Achieved}_{Frames}}{\text{Total}_{Frames}} * 100\%,$$

wherein $\text{Achieved}_{frames}$ comprises all exercise frames advanced prior to the frame duration and $\text{Total}_{frames}$ comprises the total number of exercise frames in the exercise; and
an accuracy rule comprising calculating an accuracy according to:

$$\text{Accuracy} = \frac{\text{Total}_{Frames}}{\text{Total}_{Frames} + \text{Stuck}_{Frames}} * 100\%,$$

wherein $\text{Stuck}_{frames}$ comprises the number of exercise frames advanced after a display time exceeding the frame duration.

16. The physical therapy administration system of claim 1, wherein the CRM comprises a performance module to calculate at least one performance score for the patient response according to at least one scoring rule; and a monitoring module to review the patient response and the at least one performance score.

\* \* \* \* \*